(12) United States Patent
Freeman

(10) Patent No.: US 7,279,616 B2
(45) Date of Patent: Oct. 9, 2007

(54) METHOD FOR IMPROVING CORN STARCH EXTRACTABILITY

(75) Inventor: Judy Patricia Freeman, Cambridge (GB)

(73) Assignee: Biogemma (FR)

( * ) Notice: Subject to any disclaimer, the term of this patent is extended or adjusted under 35 U.S.C. 154(b) by 30 days.

(21) Appl. No.: 10/526,716

(22) PCT Filed: Sep. 5, 2003

(86) PCT No.: PCT/IB03/03765

§ 371 (c)(1),
(2), (4) Date: Mar. 4, 2005

(87) PCT Pub. No.: WO2004/022759

PCT Pub. Date: Mar. 18, 2004

(65) Prior Publication Data

US 2005/0246792 A1 Nov. 3, 2005

Related U.S. Application Data

(60) Provisional application No. 60/407,976, filed on Sep. 5, 2002.

(30) Foreign Application Priority Data

Sep. 5, 2002 (EP) ................................. 02292190

(51) Int. Cl.
*C12N 15/82* (2006.01)
*C12N 15/00* (2006.01)
*C12N 15/29* (2006.01)
*C12N 15/63* (2006.01)
*A01H 5/00* (2006.01)

(52) U.S. Cl. ...................... 800/284; 800/278; 800/287; 800/300.1; 435/468; 435/412; 435/320.1; 536/23.1; 536/23.2; 536/23.6; 536/24.1

(58) Field of Classification Search ..................... None
See application file for complete search history.

(56) References Cited

U.S. PATENT DOCUMENTS 4,407,956 A   10/1983  Howell
6,353,154 B1 *  3/2002  Kossmann et al. ......... 800/284

FOREIGN PATENT DOCUMENTS

WO   WO9961580     * 12/1999
WO   WO-01/98509     12/2001
WO   WO-02/086130 A2 10/2002

OTHER PUBLICATIONS

Morris et al 2002, Plant Molecular Biology 48: 633-647, pp. 641 and 643.*

Lillemo, M. et al., "A leucine to proline mutation in puroindoline b is frequently present in hard wheats from Northern Europe", Theoretical and Applied Genetics, vol. 100, No. 7, pp. 1102-1107, May 2000.
Krishnamurthy, K. et al., "Expression of wheat puroindoline genes in transgenic rice enhances grain softness", Nature Biotechnology, vo. 19, No. 2, , pp. 162-166, Feb. 2001.
Singh, N. et al., "West Milling of Corn—A Review of Laboratory-Scale and Pilot Plant-Scale Procedures", American Association of Ceral Chemists, Inc., vol. 73, No. 6, pp. 659-667, 1996.
Giroux, M. et al., "Wehat grain hardness results from highly conserved mutations in the friabilin components puroindoline a and b", Proceedings of the National Academy of Sciences USA, vol. 95, pp. 6262-6266, May 1998.
Gautier, M.-F. et al., "Triticum aestivum puroindolines, two basic cystine-rich seed proteins: cDNA sequence analysis and developmental gene expression", Plant Molecular Biology, vol. 25, pp. 43-57, 1994.
An, G. "Development of Plant Promoter Expression Vectors and Their Use for Analysis of Differential Activity of Napoline Synthase Promoter in Transformed Tobacco Cells", Plant Physiol., vol. 81, pp. 86-91, 1986.
Anderson, O.D. et al., "The characterization and compartive analysis of high-molecular-weight glutenin genes from genomes A and B of a hexaploid bread wheat", Theor Appl Genet, vol. 77, pp. 689-700, 1989.
Allison, R. et al., "The Nucleotide Sequence of the Coding Region of Tobacco Etch Virus Genomic RNA: Evidence for the Synthesis of a Single Polyprotein", Virology, vol. 154, pp. 9-20, 1986.
Armstrong, C., "Regeneration of Plants from Somatic Cell Cultures: Applications for in vitro Genetic Manipulation", in M. Freleng and V. Walbot, eds. *The Maize Handbook*, Springer-Verlag, New York, Inc., pp. 663-671, 1994.
Bevan, M.W., et al., "A chimaeric antibiotic resistance gene as a selectable marker for plant cell transformation", Nature, vol. 304, pp. 184-187, Jul. 14, 1983.
Bevan, M., "Binary *Agrobacterium* vectors for plant transformation" Nucleic Acids Research, vol. 12, No. 22, pp. 8711-8721, 1984.
Callis, J. et al., "Introns increase gene expression in cultured maize cells", Genes & Development, vol. 1, pp. 1183-1200, 1987.
Cao, J. et al., "Regenreation of herbicide resistant transgenic rice plants following microprojectile-mediated transformation of suspension culture cells", Plant Cell Reports, vol. 11, pp. 586-591, 1992.
Carrington, J.C. et al., "Cap-Independent Enhancement of Translation by a Plant Polyvirus 5' Nontranslated Region", Journal of Virology, vol. 64, No. 4, pp. 1590-1597, Apr. 1990.
Christensen, A.H. et al., "Ubiquitin promoter-based vectors for high-level expression of selectable and/or screenable marker genes in monocotyledonous plants", Transgenic Research, vol. 5, pp. 213-218, 1996.

(Continued)

Primary Examiner—Russell P. Kallis
Assistant Examiner—Brent T Page
(74) Attorney, Agent, or Firm—Connolly Bove Lodge & Hutz LLP

(57) ABSTRACT

The present invention relates to the transformation of maize with a grain softness-enhancing gene for improving starch extractability. The invention more precisely concerns the reduction of wet milling time using genetically transformed corn that expresses puroindoline.

7 Claims, 4 Drawing Sheets

OTHER PUBLICATIONS

Davies, J. et al., "Plasmid-Determined Resistance to Antimicrobial Agents", Ann. Rev. Microbiol., vol. 32, pp. 469-518, 1978.

Dekeyser, R. et al., "Evaluation of Selectable Markers for Rice Transformation", Plant Physiol., vol. 90, pp. 217-223, 1989.

Della-Cioppa, G. et al; "Protein Trafficking in Plant Cells", Plant Physiol., vol. 84, pp. 965-968, 1987.

Depicker, A. et al., "Nopaline Synthase: Transcrip Mapping and DNA Sequence", Journal of Molecular and Applied Genetics, vol. 1, pp. 561-573, 1982.

Breyne, P. et al., "Effect of T-DNA configuration on transgene expression", Mol. Gen. Genet., vol. 235, pp. 389-396, 1992.

Dipegny-This, D. et al., "The cruciferin gene family in radish", Plant Molecular Biology, vol. 20, pp. 467-479, 1992.

Koziel, M. et al., "A cauliflower mosaic virus promoter directs expression of kanamycin resistance in morphogenic transformed plant cells", Journal of Molecular and Applied Genetics, vol. 2, pp. 549-562, 1984.

Eichholtz, D.A. et al., "Expression of mouse dihydrofolate reductase gene confers methotrexate resistance in transgenic petunia plants", Somatic Cell and Molecular Genetics, vol. 13, No. 1, pp. 67-76, 1987.

Elroy-Stein, O. et al., "Cap-independent translation of mRNA conferred by encephalomyocarditis virus 5' sequence improves the performance of the vaccinia virus/bacteriophage T7 hybrid expression system", Proc. Natl. Acad. Sci. USA, vol. 86, pp. 6126-6130, Aug. 1989.

Fraley, R. et al., "Expression of bacterial genes in plant cells", Proc. Natl. Acad. Sci. USA, vol. 80, pp. 4803-4807, Aug. 1983.

Franck, F. et al., "Nucleotide Sequence of Cauliflower Mosaic Virus DNA", Cell, vol. 21, pp. 285-294, Aug. 1980.

Fromm, M. et al., "Expression of genes transferred into monocot and dicot plant cells by electroporation", Proc. Natl. Acad. Sci. USA, vol. 82, pp. 5824-5828, Sep. 1985.

Gallie, D.R. et al., "Eukaryotic viral 5'-leader sequences acta as translational enhancers in eukaryotes and prokaryotes", Molecular Biology of RNA, pp. 237-258, 1989.

Gautier, M.-F. et al., "Triticum aestivum puroindolines, two basic cystine-rich seed proteins: cDNA sequence analysis and development gene expression", Plant Molecular Biology, vol. 25, pp. 43-57, 1994.

Giroux, M.J. et al., "Wheat grain hardness results from highly conserved mutations in the friabilin components puroindoline a and b", Proc. Natl. Acad. Sci. USA, vol. 95, pp. 6262-6266, May 1998.

Gritz, L. et al., "Plasmid-encoded hygromycin B resistance: the sequence of hygromycin B. phosphotransferase gene and its expression in *Esherichia coli* ad *Saccharomyces cerevisiae*", Gene, vol. 25, pp. 179-188, 1983.

Halford, N.G. et al., "Functional analysis of the upstream regions of a silent and an expressed member of a family of wheat seed protein genes in transgenic tobacco", Plant Science, vol. 62, pp. 207-216, 1989.

Hauptmann, R.M. et al., "Evaluation of Selectrable Markers for Obtaining Stable Transformants in the Gramineae", Plant Physiol., vol. 86, pp. 602-606, 1988.

Herrera-Estrella, L. et al., "Chrimeric genes as dominant selectable markers in plant cells", The EMBO Journal, vol. 2, No. 6, pp. 987-995, 1983.

Hiei, Y. et al., "Efficient transformation of rice (*Oryza sativa L.*) mediated by *Agrobacterium* and sequence analysis of the boundaries of the T-DNA", The Plant Journal, vol. 6, No. 2, pp. 271-282, 1994.

Hoekema, A. et al., "A binary plant vector strategy based on separation of vir- and T-region of the *Agrobacterium tumefaciens* Tri-plasmid", Nature, vol. 303, May 12, 1983.

Hohn, B. et al., Chapter 22, "Cauliflower Mosaic Virus: A Potential Vector for Plant Genetic Engineering", Molecular Biology of Plant Tumors, Academic Press, Inc., pp. 549-560, 1982.

Horsch, R.B. et al., "Inheritance of Functional Foreign Genes in Plants", Science, vol. 223, pp. 496-498, Feb. 3, 1984.

Ishida, Y. et al., "High efficiency transformation of maize (*Zea mays L.*) mediated by *Agrobacterium tumefaciens*", Nature Biotechnolgoy, vol. 14, pp. 745-750, Jun. 1996.

Jobling, S.A. et al., "Enhanced translation of chimaeric messenger RNAs containing a plant viral untranslated leader sequence", Nature, vol. 325, pp. 622-625, Feb. 12, 1987.

Jouanin, L. et al., "Transfer of A 4.3kb fragment of the TL-DNA of *Agrobacterium rhizohenes* strain A4 confers the pRi transformed phenotype to regenerated tobacco plants", Plant Science, vol. 53, pp. 53-63, 1987.

Kay, R. et al., "Duplication of CaMV 35S Promoter Sequences Creates a Strong Enhancer for Plant Genes", Science, vol. 236, pp. 1299-236, Jun. 5, 1987.

Lommel, S.A. et al., "Identification of the Maize Chlorotic Mottle Virus Capsid Protein Cistron and Characterization of its Subgenomic Messenger RNA", Virology, vol. 181, pp. 382-385, 1991.

Maas, C. et al., "The combination of a novel stimulatory element in the first exon of the maize Shrunken-1 gene with the following intron 1 enhances reporter gene expression up to 1000-fold", Plant Molecular Biology, vol. 16, pp. 196-207, 1991.

Macejak, D.G. et al., "Internal initiation of translation mediated by the 5' leader of a cellular mRNA", Nature, vol. 353, pp. 90-94, Sep. 5, 1991.

Mattanovich, D. et al., "Efficient transformation of *Agrobacterium spp.* by electroporation", Nucleic Acids Research, vol. 17, No. 16, p. 6747, 1989.

McCormick, S. et al., "Leaf disc transformation of cultivated tomato (*L. esculentum*) using *Agrobacterium tumefaciens*", Plant Cell Reports, vol. 5, pp. 81-84, 1986.

McElroy, D. et al., "Isolation of an Efficient Actin Promoter for Use in Rice Transformation", The Plant Cell, vol. 2, pp. 163-171, Feb. 1990.

McElroy, D. et al., "Construction of expression vectors based on the rice actin 1 (Act1) 5' region for use in monocot transformation", Mol. Gen. Genet., vol. 231, pp. 150-160, 1991.

Meijer, E.G.M. et al., "Transgenic rice cell lines and plants: expression of transferred chimeric genes", Plant Molecular Biology, vol. 16, pp. 807-820, 1991.

Morris, B.A.M. et al., "The nucleotide sequence of the infectious cloned DNA component of tobacco yellow dwarf virus reveals features of geminiviruses infecting monocotyledonous plants", Virology, vol. 187, pp. 633-642, 1992.

Mullis, K.B. et al., "Specific Synthesis of DNA in Vitro via a polymerase-catalyzed chain reaction", Methods in Enzymology, vol. 155, pp. 335-350, Sep. 21, 1998.

Ohta, S. et al., "Construction and Expression in Tobacco of a B-Glucuronidase (GUS) Reporter Gene Containing an Intron Within the Coding Sequence", Plant Cell Physiol, vol. 31, No. 6, pp. 805-813, 1990.

Paszkowski, J. et al., "Direct gene transfer to plants", The EMBO Journal, vol. 3, No. 12, pp. 2717-2722, 1984.

Robert, L.S. et al., "Tissue-Specific Expression of a Wheat High Molecular Weight Glutenin Gene in Transgenic Tobacco", The Plant Cell, vol. 1, pp. 569-578, Jun. 1989.

Sambrook et al., "Hybridization of Radiolabeled Probes to Immobilized Nucleic Acids, Analysis and Cloning oe Eukaryotic Genomic DNA", *Molecular Cloning, A Laboratory Manual*, Cold Spring Harbor Laboratory Press, 1989, pp. 9.47-9.62.

Snowden, K.C. et al., "Intron position affects expression from the tpi promoter in rice", Plant Molecular Biology, vol. 31, pp. 689-692, 1996.

Southern, E.M., "Detection of Specific Sequences Among DNA Fragments Separated by Gel Electrophoresis", J. Mol. Biol., vol. 98, pp. 503-517, 1975.

Vancanneyt, G. et al., "Construction of an intron-containing marker gene: Splicing of the intron in transgenic plants and its use in monitoring early events in *Agrobacterium*-mediated plant transformation", Mol. Gen. Genet., vol. 220, p. 245-250, 1990.

Vain, P. et al., "Enhancement of production and regeneration of embryogenic type II callus in *Zea mays L.* by AgNO3", Plant Cell, Tissue and Organ Culture, vol. 18, pp. 143-151, 1989.

Waldron, C. et al., "Resistance to hygromycin B", Plant Molecular Biology 5, vol. 103, pp. 103-108, 1985.

White, J. et al., "A cassette containing the bar gene of *Streptomyces hygroscopicus*: a selectable marker for plant transformation", Nucleic Acids Research vol. 18, No. 4, p. 1062, Dec. 18, 1989.

Yoder, J.I. et al., "Transformation Systems for Generating Marker-Free Transgenic Plants", Bio/Technology, vol. 12, pp. 263-267, 1994.

Zambryski, P. et al., "Transfer and Function to T-DNA Genes from *Agrobacterium* Ti and Ri Plasmids in Plants", Cell, vol. 56, pp. 193-201, Jan. 27, 1989.

Greenblatt, G.A. et al., "Relationship Between Endosperm Texture and the Occurrence of Friabilin and Bound Polar Lipids on Wheat Starch", Cereal Chemistry, vol. 72, pp. 172-176, 1995.

* cited by examiner

SEQUENCE LISTING

```
<160> NUMBER OF SEQ ID NOS: 5

<210> SEQ ID NO 1
<211> LENGTH: 598
<212> TYPE: DNA
<213> ORGANISM: Triticum aestivum
<220> FEATURE:
<221> NAME/KEY: CDS
<222> LOCATION: (17)..(463)

<400> SEQUENCE: 1
aaacaacatt gaaaac atg aag acc tta ttc ctc cta gct ctc ctt gct ctt        52
               Met Lys Thr Leu Phe Leu Leu Ala Leu Leu Ala Leu
                 1               5                  10 gta gcg agc aca acc ttc gcg caa tac tca gaa gtt ggc ggc tgg tac         100
Val Ala Ser Thr Thr Phe Ala Gln Tyr Ser Glu Val Gly Gly Trp Tyr
        15                  20                  25 aat gaa gtt ggc gga gga ggt ggt tct caa caa tgt ccg cag gag cgg         148
Asn Glu Val Gly Gly Gly Gly Gly Ser Gln Gln Cys Pro Gln Glu Arg
 30                  35                  40 ccg aag cta agc tct tgc aag gat tac gtg atg gag cga tgt ttc aca         196
Pro Lys Leu Ser Ser Cys Lys Asp Tyr Val Met Glu Arg Cys Phe Thr
 45                  50                  55                  60 atg aag gat ttt cca gtc acc tgg ccc aca aaa tgg tgg aag ggc ggc         244
Met Lys Asp Phe Pro Val Thr Trp Pro Thr Lys Trp Trp Lys Gly Gly
                 65                  70                  75 tgt gag cat gag gtt cgg gag aag tgc tgc aag cag ctg agc cag ata         292
Cys Glu His Glu Val Arg Glu Lys Cys Cys Lys Gln Leu Ser Gln Ile
             80                  85                  90 gca cca caa tgt cgc tgt gat tct atc cgg cga gtg atc caa ggc agg         340
Ala Pro Gln Cys Arg Cys Asp Ser Ile Arg Arg Val Ile Gln Gly Arg
         95                  100                 105 ctc ggt ggc ttc ttg ggc att tgg cga ggt gag gta ttc aaa caa ctt         388
Leu Gly Gly Phe Leu Gly Ile Trp Arg Gly Glu Val Phe Lys Gln Leu
     110                 115                 120 cag agg gcc cag agc ctc ccc tca aag tgc aac atg ggc gcc gac tgc         436
Gln Arg Ala Gln Ser Leu Pro Ser Lys Cys Asn Met Gly Ala Asp Cys
125                 130                 135                 140 aag ttc cct agt ggc tat tac tgg tga tgatatagcc tctattcgtg              483
Lys Phe Pro Ser Gly Tyr Tyr Trp
                 145 ccaataaaat gtcacatatc atagcaagtg gcaaataaga gtgctgagtg atgatctatg      543 aataaaatca cccttgtata ttgatctgtg ttcgagaaaa aaaaaaaaa aaaaa            598

<210> SEQ ID NO 2
<211> LENGTH: 148
<212> TYPE: PRT
<213> ORGANISM: Triticum aestivum

<400> SEQUENCE: 2
```

```
Met Lys Thr Leu Phe Leu Leu Ala Leu Leu Ala Leu Val Ala Ser Thr
1               5                   10                  15

Thr Phe Ala Gln Tyr Ser Glu Val Gly Gly Trp Tyr Asn Glu Val Gly
            20                  25                  30

Gly Gly Gly Ser Gln Gln Cys Pro Gln Glu Arg Pro Lys Leu Ser
        35                  40                  45

Ser Cys Lys Asp Tyr Val Met Glu Arg Cys Phe Thr Met Lys Asp Phe
    50                  55                  60

Pro Val Thr Trp Pro Thr Lys Trp Lys Gly Gly Cys Glu His Glu
65              70                  75                  80

Val Arg Glu Lys Cys Lys Gln Leu Ser Gln Ile Ala Pro Gln Cys
                85                  90                  95

Arg Cys Asp Ser Ile Arg Arg Val Ile Gln Gly Arg Leu Gly Gly Phe
                100                 105                 110

Leu Gly Ile Trp Arg Gly Glu Val Phe Lys Gln Leu Gln Arg Ala Gln
            115                 120                 125

Ser Leu Pro Ser Lys Cys Asn Met Gly Ala Asp Cys Lys Phe Pro Ser
    130                 135                 140

Gly Tyr Tyr Trp
145

<210> SEQ ID NO 3
<211> LENGTH: 680
<212> TYPE: DNA
<213> ORGANISM: Triticum aestivum
<220> FEATURE:
<221> NAME/KEY: CDS
<222> LOCATION: (25)..(471)

<400> SEQUENCE: 3
cctgcaccaa aacacactga caac atg aag gcc ctc ttc ctc ata gga ctg          51
                         Met Lys Ala Leu Phe Leu Ile Gly Leu
                         1               5 ctt gct ctg gta gcg agc acc gcc ttt gcg caa tat agc gaa gtt gtt        99
Leu Ala Leu Val Ala Ser Thr Ala Phe Ala Gln Tyr Ser Glu Val Val
10                  15                  20                  25 ggc agt tac gat gtt gct ggc ggg ggt ggt gct caa caa tgc cct gta       147
Gly Ser Tyr Asp Val Ala Gly Gly Gly Gly Ala Gln Gln Cys Pro Val
                30                  35                  40 gag aca aag cta aat tca tgc agg aat tac ctg cta gat cga tgc tca       195
Glu Thr Lys Leu Asn Ser Cys Arg Asn Tyr Leu Leu Asp Arg Cys Ser
            45                  50                  55 acg atg aag gat ttc ccg gtc acc tgg cgt tgg tgg aaa tgg tgg aag       243
Thr Met Lys Asp Phe Pro Val Thr Trp Arg Trp Trp Lys Trp Trp Lys
        60                  65                  70 gga ggt tgt caa gag ctc ctt ggg gag tgt tgc agt cgg ctc ggc caa       291
Gly Gly Cys Gln Glu Leu Leu Gly Glu Cys Cys Ser Arg Leu Gly Gln
75                  80                  85 atg cca ccg caa tgc cgc tgc aac atc atc cag ggg tca atc caa ggc       339
Met Pro Pro Gln Cys Arg Cys Asn Ile Ile Gln Gly Ser Ile Gln Gly
90                  95                  100                 105 gat ctc ggt ggc atc ttc gga ttt cag cgt gat cgg gca agc aaa gtg       387
Asp Leu Gly Gly Ile Phe Gly Phe Gln Arg Asp Arg Ala Ser Lys Val
                110                 115                 120 ata caa gaa gcc aag aac ctg ccg ccc agg tgc aac cag ggc cct ccc       435
Ile Gln Glu Ala Lys Asn Leu Pro Pro Arg Cys Asn Gln Gly Pro Pro
            125                 130                 135 tgc aac atc ccc ggc act att ggc tat tac tgg tga tgtagcttcc            481
Cys Asn Ile Pro Gly Thr Ile Gly Tyr Tyr Trp
```

-continued

```
           140             145
atttatgact agctaataaa ctgtcacata ccactgcgtg tgacaaataa aagtggtcat    541
ggaataattt atgaataaaa tttcagcatg tgcctgcgcg aggtgtctat agcaaacata    601
tcagtatgcc tatatatgtt aatcaagata gcaatgttca catacaaaaa aaaaaaaaaa    661
aaaaaaaaaa aaaaaaaaa                                                 680

<210> SEQ ID NO 4
<211> LENGTH: 148
<212> TYPE: PRT
<213> ORGANISM: Triticum aestivum

<400> SEQUENCE: 4

Met Lys Ala Leu Phe Leu Ile Gly Leu Leu Ala Leu Val Ala Ser Thr
1               5                   10                  15

Ala Phe Ala Gln Tyr Ser Glu Val Val Gly Ser Tyr Asp Val Ala Gly
            20                  25                  30

Gly Gly Gly Ala Gln Gln Cys Pro Val Glu Thr Lys Leu Asn Ser Cys
        35                  40                  45

Arg Asn Tyr Leu Leu Asp Arg Cys Ser Thr Met Lys Asp Phe Pro Val
    50                  55                  60

Thr Trp Arg Trp Trp Lys Trp Lys Gly Gly Cys Gln Glu Leu Leu
65                  70                  75                  80

Gly Glu Cys Cys Ser Arg Leu Gly Gln Met Pro Pro Gln Cys Arg Cys
                85                  90                  95

Asn Ile Ile Gln Gly Ser Ile Gln Gly Asp Leu Gly Gly Ile Phe Gly
            100                 105                 110

Phe Gln Arg Asp Arg Ala Ser Lys Val Ile Gln Glu Ala Lys Asn Leu
        115                 120                 125

Pro Pro Arg Cys Asn Gln Gly Pro Pro Cys Asn Ile Pro Gly Thr Ile
    130                 135                 140

Gly Tyr Tyr Trp
145

<210> SEQ ID NO 5
<211> LENGTH: 16
<212> TYPE: DNA
<213> ORGANISM: Artificial
<220> FEATURE:
<223> OTHER INFORMATION: oligonucleotide

<400> SEQUENCE: 5
tcgacccacg cgtccg                                                    16
```

METHOD FOR IMPROVING CORN STARCH EXTRACTABILITY

RELATED APPLICATIONS

This application is a national stage application (under 35 U.S.C. 371) of PCT/IB2003/003765 filed Sep. 5, 2003 which claims benefit to European application 02292190.2 filed Sep. 5, 2002 and U.S. application Ser. No. 60/407,976 filed Sep. 5, 2002.

FIELD OF THE INVENTION

The present invention relates to the transformation of maize with a grain softness-enhancing gene, such as a puroindoline, for improving corn starch extractability. The invention more particularly concerns the reduction of wet milling time using genetically transformed corn that expresses puroindoline.

BACKGROUND OF THE INVENTION

Corn kernels have three main parts, the seed coat or pericarp, the starchy endosperm, and the embryo, commonly called the germ. The pericarp is the outer skin or hull of the kernel which serves to protect the seed. The endosperm, the main energy reserve, makes up about 80% of the total weight of the kernel. It is about 90% starch and 7% gluten (protein), with the remainder consisting of small amounts of oil, minerals and some trace constituents. The embryo contains a miniature plant made up of a root-like portion and five or six embryonic leaves. In addition, there are large quantities of high energy oil to feed the tiny plant when it starts to grow, as well as many substances required during germination and early development.

Starch is one of nature's major renewable resources and a mainstay of food and industrial economy. Basic consumer necessities such as paper and textiles are major uses for corn starch in sizing, surface coating and adhesive applications.

For more than 150 years, corn refiners have been perfecting the process of separating corn into its component parts to create a myriad of value added products. The corn wet milling process separates corn into four main components: starch, germ, fiber and protein.

An overview of wet milling process is illustrated in the FIG. 4 annexed herewith. Typically, the process comprises five basic steps:
  cleaning;
  steeping;
  germ separation;
  grinding and screening; and
  starch separation.

The first step in the process consists in cleaning the grain to remove extraneous material such as pieces of cob, foreign seeds, fine dirt, and other light unwanted material.

The cleaned corn is further soaked in 50 degree water, usually containing small quantities of dissolved sulfur dioxide to prevent excessive bacterial growth, for 30 to 40 hours in steep tanks. During "steeping", the kernels absorb water, increasing their moisture levels from 15 percent to 45 percent and more than doubling in size. As the corn swells and softens, the mild acidity of the steepwater begins to loosen the gluten bonds within the corn and release the starch. After steeping, the corn is coarsely ground to break the germ loose from other components.

Water is added to the attrition mills and a thick slurry of macerated kernels and whole germ results. Because the germ at this stage contains 40-50% oil (about 85% of total corn oil) it is lighter than the endosperm and hull. The "germ separation" is thus achieved using centrifugal force to isolate the germ.

The remaining mixture of hull and endosperm then passes through a series of "grinding" and "screening" operations to release the starch and gluten from the fiber In the kernel. The suspension of starch, gluten and fiber is flowed over fixed screens which catch fiber but allow starch and gluten to pass through.

The water slurry of starch and gluten is further separated by centrifugation. Because starch and gluten differ in density, almost complete "starch separation" is obtained. The starch, with just one or two percent protein remaining, is diluted, washed 8 to 14 times, rediluted and washed again to remove the last trace of protein and produce highly pure starch.

Typical operations yield a starch stream over 99% pure starch, usually more than 99.5% pure starch. The overall yield of the wet milling process is at least 95% of starch initially present in corn grain.

The time required to conduct the totality of these operations is in theory up to 48 hours. In practice, many millers claim it usually takes about 36 hours or more to them to get over 95% of the starch out through this process.

A reduction of the milling time while maintaining same starch yield would be of great industrial interest. Actually, such a reduction would increase milling plants capacity and thus reduce cost per unit of starch extracted.

SUMMARY OF THE INVENTION

The inventors propose to improve starch extractability by reducing the adhesion between the starch granules and the protein matrix in the maize endosperm. An easy way to determine this reduction of adhesion is through measuring grain hardness, which is related to the density of starch protein matrix in the endosperm. The inventors further observed that in harder grain it takes longer to hydrate the starch in the steeping step to a given moisture, and to wash it in the starch separators.

Accordingly, the invention relates to a method for improving corn starch extractability in a given time frame in the course of wet milling process. Actually, starch extractability was found to be improved in corn with increased grain softness, such as obtainable with corn expressing a puroindoline protein. Puroindoline expressing corn indeed allows faster hydration and easier starch protein separation, decreased washings in the extraction process.

DETAILED DESCRIPTION OF THE INVENTION

Definitions

Figure 1:
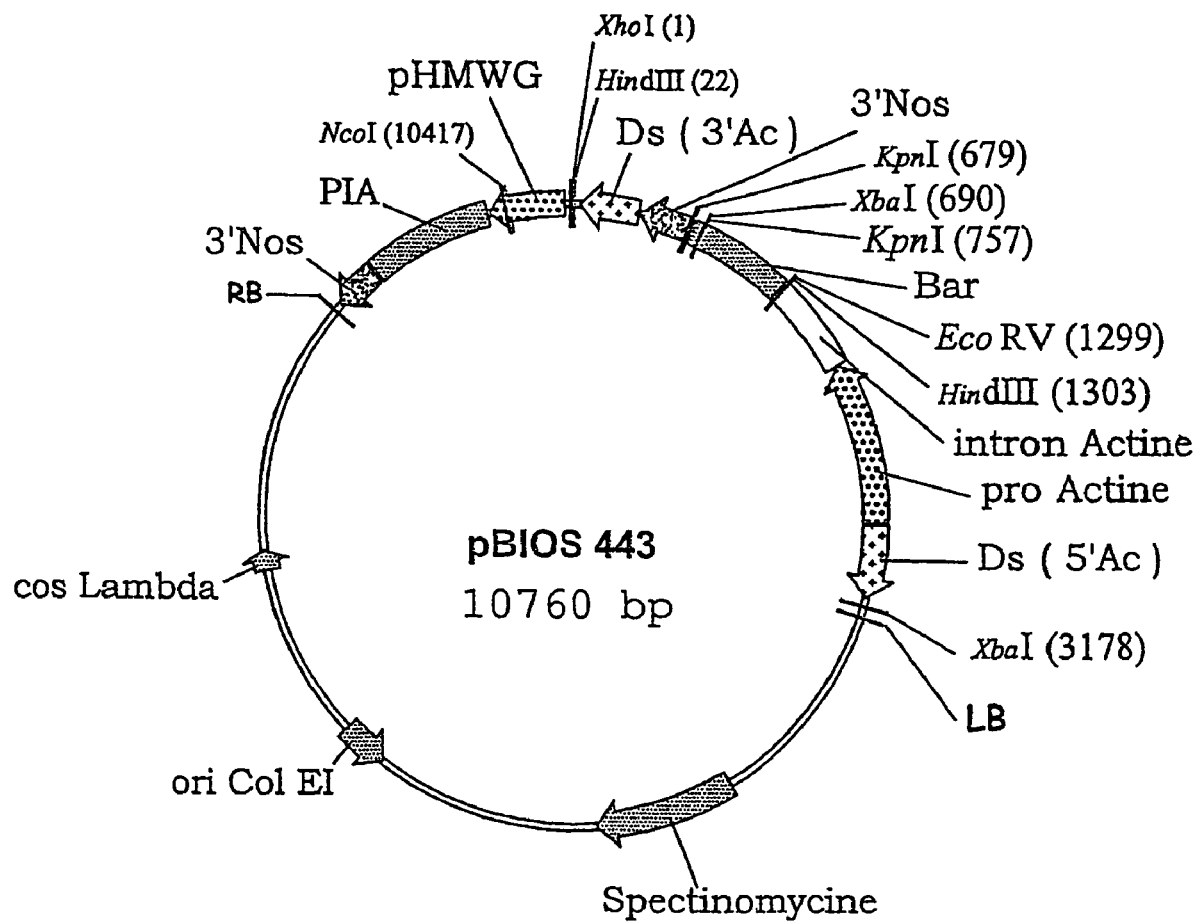
FIG. 1 represents plasmid pBIOS 443 which contains the puroindoline-a cassette.

In the context of the present invention, the term "plant" refers to maize.

In the present application, "increasing grain softness" or "increased grain softness" means making the texture of the corn grain softer as compared to wild-type corn that does not express a grain softness-enhancing gene. A "grain softness-enhancing gene" is meant for a gene whose expression in transformed maize leads to grain texture softening. In particular, grain softness-enhancing genes include puroindoline-a and puroindoline-b.

One skilled in the art can readily assess grain softness by techniques of hardness measurement, such as Near Infra-Red (NIR) spectrophotometry or Single kernel hardness readings (SKCS). Briefly, SKCS are obtained by analysing 10 individual kernels each of transgenic samples for hardness using the 4100 SKCS model from Perten Instruments following the manufacturer's operation manual. The 4100 singulates individual kernels, weighs them, then crushes them between a toothed rotor and a progressively narrowing crescent gap. As a kernel is crushed, the force between the rotor and crescent are also measured. This information is processed to provide weight, size, moisture and hardness information on individual kernel basis. Mean hardness index, weight, size, moisture and their standard deviations are calculated from the single kernel data obtained on a 300 kernel sample. Hardness classification is determined from the average hardness index of the sample and the distribution of individual kernel hardness measurements within four hardness ranges as defined by the USDA/GIPSA. Hardness can further be measured by a NIR spectrophotometer, with a laboratory Mill 3100 from Perten Instrument and an Inframatic 8100 Perten spectrophotometer. The machine is calibrated with references samples analysed by the reference laboratory in France for the infra red method for hardness determination: ITCF laboratory (Paris).

The term "maize with increased grain softness" describes a maize genetically transformed to stably express a grain softness-enhancing gene such as puroindoline. Expression of said gene confers a soft texture to the corn produced by said genetically transformed maize, and reduces the adhesion between the starch granules and the protein matrix in the maize endosperm.

The term "puroindoline" denotes puroindoline-a, puroindoline-b or homolog thereof. Preferably said puroindoline is puroindoline-b. The encoding precursors and amino acid sequences of puroindoline-b (SEQ ID N°1 and SEQ ID N°2, respectively—accession number X69912) and puroindoline-a (SEQ ID N°3 and SEQ ID N°4, respectively—accession number X69913) have been described by Gautier (1994) and are shown in the annexed sequence listing. "puroindoline homolog" refers to any isolated puroindoline gene sequence exhibiting the same activity in terms of modification of grain texture even if the DNA sequence is not exactly identical. Puroindoline cDNA or gene sequences present in the same species and/or homologs of the puroindoline gene present in other plant species can be identified and readily Isolated without undue experimentation. Also cDNA libraries can be obtained from mRNA from plant cell lines or tissues known or suspected to express a puroindoline.

The term "homology" generally refers to nucleic sequences that are different from a given gene sequence by substitution, deletion and/or insertion of nucleotides such that the nucleotide sequence encodes a protein with substantial homology to that encoded by said gene sequence. Preferably such a homologous nucleic acid sequence is at least 75% identical to the puroindoline gene sequence, preferably at least 85% identical, more preferably at least 90, 95, 98% identical.

A percentage of identity between two nucleic sequences refers to the percentage of nucleotides identical between the two nucleic sequences, these sequences being optimally aligned. The percentage is statistical. The optimal alignment for the comparison may be obtained for instance by the algorithm of local homology of Smith and Waterman (1981), or of Neddleman and Wunsch (1970), or by softwares using these algorithms (GAP, BESTFIT, BLAST).

In a preferential manner such a homologous nucleic acid sequence hybridizes to the complementary sequence of the puroindoline gene sequence under stringent conditions. The parameters defining the stringency conditions depend on the temperature in which 50% of the coupled strands separate (Tm).

Concerning the sequences comprising more than 30 bases, Tm is defined by the relation Tm=81.5+0.41 (% G+C)+16.6 Log (concentration in cations)−0.63 (% formamide)−(600/numbers of bases). (Sambrook et al., 1989).

Concerning the sequences less long than 30 bases, Tm is defined by the relation Tm=4(G+C)+2(A+T).

In appropriate stringency conditions, in which non-specific sequences do not hybridize, the temperature of hybridization is approximately between 5 and 30° C., preferable between 5 and 10° C. under Tm and hybridization buffers used are preferably solutions of higher ionic force like a solution 6*SSC for example.

For the purpose of the invention, a "probe" or "primer" is defined as being a single-stranded nucleic acid fragment or a denatured double-stranded fragment comprising, for example, from 12 bases to a few kb, in particular from 15 to a few hundred bases, preferably from 15 to 50 or 100 bases, and having a specificity of hybridisation under given conditions so as to form a hybridisation complex with a target nucleic acid.

As used herein, "improving corn starch extractability" or "improved process of extracting corn starch" denotes an increase in starch extraction yield through wet milling process in a given time frame, as compared to corn from a wild-type maize that does not express a grain softness-enhancing gene.

More particularly, the improvement may consist in a reduction of the steeping time necessary to hydrate the starch to a given moisture. Typically, in the art it takes 30 to 40 hours to obtain kernels with 45% moisture. As to starch with improved extractability, the steeping time is preferably reduced by at least 10%, preferably at least 30%, still preferably by at least 50%. Preferably, in the milling process of the invention, the steeping step may be carried out in 24 hours or less.

In the context of the invention, the "steeping step time" or "steeping time" is defined as the time necessary to increase the moisture level of corn kernel to about 45 percent and/or to double their size by soaking the kernels in 50 degree water. Measurement of moisture degree or kernel volume can be readily achieved with ordinary knowledge of the skilled in the art.

In the context of the invention, the "number of washes in the starch separation step" is defined as the number of washes necessary to obtain a starch with a purity degree of at least 99%, preferably at least 99.5%.

Production of Maize with Increased Grain Softness

So far, crops users have only been concerned with grain hardness of wheat. Although best known for its gluten-forming properties, the primary basis for discriminating different end uses in wheat is not protein content but grain hardness. Grain hardness refers to the texture of the kernel (caryopsis), that is, whether the endosperm is physically hard or soft.

Friabilin and grain softness protein are two proteins isolated from wheat starch granules whose presence has been correlated with grain softness. Friabilins are marker proteins for grain softness. Puroindolines are low molecular weight basic cystine-rich proteins found in wheat seeds. Puroindolines show identity to the N-terminal sequence of friabilins.

Two highly conserved mutations in puroindoline-a and puroindoline-b have been found to be inseparably linked to grain hardness (Giroux M. J. and Morris C. F., 1998). It was reported that the absence of puroindoline-a protein and transcript and a glycine-to-serine mutation in puroindoline-b are two highly conserved mutations associated with grain hardness.

Isolation and characterization of puroindoline-a and -b, have been described in Gautier M-F et al (1994). In wheat, an inverse relationship between hardness and puroindoline content has been demonstrated (Dubreil L. et al., 1998). In particular, expression of puroindoline-b is associated with increased grain softness.

Native maize does not express puroindolines. The production of maize plants which express puroindolines has never been reported nor demonstrated to be achievable reproducibly. Such plants may be produced according to the method described hereafter.

A method of producing a maize with increased grain softness may comprise the steps consisting of introducing a nucleic acid sequence which encodes a puroindoline protein into at least a maize cell and cultivating such transformed cell in conditions for regenerating fertile stable transformed maize plant. More particularly, said method comprises the steps consisting of:

(a) introducing a DNA construct which allow expression of a puroindoline protein into plant cell, plant tissue, or plant, (b) selecting the plant cell, or plant tissue, or plant which stably maintain the puroindoline expression, (c) and optionally regenerating fertile stable transformed plant.

DNA Construct

Said DNA construct, or "expression cassette", may include 5' and 3' regulatory sequences operatively linked to the puroindoline gene. "Operatively linked" refers to functional linkage between the 5' and 3' regulatory sequences and the controlled nucleic acid sequence. Preferably said DNA construct is a cDNA construct The 5' regulatory sequence are notably promoters. These promoters would be selected for strength and/or spatial and temporal expression and/or inducibility. More particularly, the promoters are cell-specific, tissue-specific, organ-specific, development-specific, partially constitutive or fully constitutive (a promoter that strongly expresses in many or all plant tissues) or inducible promoters that can be expressed in a plant.

Transcription controlled by the operatively linked promoter produces a functional messenger RNA whose transcription produces the puroindoline. An expression cassette typically includes the nucleic acid sequence for puroindoline-a and/or puroindoline-b operatively linked to a transcription initiation region (a promoter sequence) and a transcription ending region (a terminator sequence).

Examples of promoters useful for plant transformation include the 35S promoter or the 19S promoter (Kay et al., 1987), the pCRV promoter (Depigny-This et al., 1992), the ubiquitin 1 promoter of maize (Christensen et al., 1996), the regulatory sequences of the T-DNA of *Agrobacterium tumefaciens*, including mannopine synthase, nopaline synthase, octopine synthase, and the promoters regulated during seed development such as the HMWG promoter (High Molecular Weight Glutenin) of wheat (Anderson O. D. et al., 1989, Roberts et al., 1989), and the waxy, zein or bronze promoters of maize.

According to a preferred method of the invention, the promoter is seed-specific and a particularly preferred method of the invention, the promoter is the HMWG promoter, for the expression cassette containing the puroindoline gene.

The expression of puroindoline-a and/or puroindoline-b may be engineered producing a plant cell transformed with nucleic acid constructs that contain multiple copies of the puroindoline gene. Alternatively, a gene encoding the desired polypeptide can be placed in a nucleic acid construct containing an amplification-selectable marker (ASM) gene such as the glutamine synthetase (GS) or dihydrofolate reductase gene. Cells transformed with such constructs are subjected to culturing regimes that select cell lines with increased copies of ASM gene. See Donn et al. (1984) for a selection protocol used to isolate of a plant cell line containing amplified copies of the GS gene. Because the desired gene is closely linked to the ASM gene, cell lines that amplified the ASM gene would also likely to have amplified the gene encoding the desired growth modulation polypeptide.

The 3' regulatory sequences are notably terminators. These 3' terminator regions are linked to the gene of interest. Among the terminators useful for plant transformation within the framework of the present invention, the ones which can be used are the polyA 35S terminator of the cauliflower mosaic virus (CaMV), described in the article of Franck et al. (1980), the NOS terminator corresponding to the region in the non coding 3' region of the nopaline synthase gene of the Ti-plasmid of *Agrobacterium tumefaciens* nopaline strain (Depicker et al. 1992), the histone terminator (EP 0 633 317), and the tmI terminator.

According to a preferred method of the invention, the terminator is the Nos terminator for the expression cassette containing the puroindoline gene.

The expression cassettes may additionally contain transit peptide sequences in the expression cassette construct. There are numerous examples in the art of transit peptides which may be used to deliver a target protein into a plastid organelle such as the small subunit (SSU) transit peptide of ribulose biphosphate carboxylase.

Other elements like introns and enhancers can also be present in the nucleic sequence of interest in order to improve the expression of the gene of interest.

An example of an enhancer is the translation activator of tobacco mosaic virus (TEV) described by Carrington and Freed (1990).

Among useful introns, the first intron of maize adh1S can be placed between the promoter and the coding sequence. This intron when included in a gene construct increased the expression of the desired protein in maize cells (Callis et al., 1987). One also can use the $1^{st}$ intron of the shrunken 1 gene of the maize (Maas et al., 1991), the $1^{st}$ intron of the catalase gene of the bean catalase (CAT-1) (Ohta et al., 1990), the $2^{nd}$ intron of the ST-LS1 gene of potato (Vancanneyt et al. 1990), the DSV intron of the yellow dwarf virus of tobacco (Morris et al., 1992), the actin-1 intron (act-1) of rice (McElroy et al., 1990) and intron 1 of triosephosphate isomerase (TPI) (Snowdon al., 1996).

The expression cassettes may additionally contain 5' leader sequences in the expression cassette construct. Such leader sequences can act to enhance translation. Such 5' leaders are known in the art and include, but are not limited to, picornavirus leaders, for example, the EMCV leader (Encephalomyocarditis 5' noncoding region) (Elroy-Stein, Fuerest, and Moss B., 1989); potyvirus leaders, for example, the TEV leader (Tobacco etch Virus) (Allison et al., 1986); the human immunoglobulin heavy-chain binding protein leader (BiP) (Macejack and Samow, 1991); the untranslated leader from the coat protein mRNA of alfalfa mosaic virus (AMV RNA 4) (Jobling and Gehrke, 1987); the tobacco mosaic virus leader (TMV) (Gallie et al., 1989); and the maize chlorotic mottle virus leader (MCMV) (Lommel et al., 1991). See also, Della-Cioppa et al. (1987). Other methods known to enhance translation can be utilized, for example introns, and the like.

In order to obtain the same modified plants, any other genes exhibiting homology or substantial homology with a puroindoline gene could be utilised as DNA sequence of interest.

The expression cassette may additionally contain at least one gene to be co-transformed into the organism. Alternatively, the additional gene(s) of interest can be provided on another expression cassette.

According to the invention, the DNA construct may contain one or several selectable markers useful for transformation and selection.

In the present invention, the terms "selectable marker", "selectable gene", "selectable marker gene", "marker gene" are used interchangeably.

These selectable markers include, but are not limited to, antibiotic resistance gene, herbicide resistance gene or visible marker genes. Other phenotypic markers are known in the art and may be used in this invention.

A number of selective agents and resistance genes are known in the art. (See, for example, Hauptmann et al., 1988; Dekeyser et al., 1988; Eichholtz et al., 1987; and Meijer et al., 1991).

Notably the selectable marker used can be the bar gene conferring resistance to bialaphos (White et al., 1990), the sulfonamide herbicide Asulam resistance gene, suI (described in WO 98/49316) encoding a type I dihydropterate synthase (DHPS), the nptII gene conferring resistance to a group of antibiotics including kanamycin, G418, paromomycin and neomycin (Bevan et al., 1983), the hph gene conferring resistance to hygromycin (Gritz et al., 1983), the EPSPS gene conferring tolerance to glyphosate (U.S. Pat. No. 5,188,642), the HPPD gene conferring resistance to isoxazoles (WO 96/38567), the gene encoding for the GUS enzyme, the green fluorescent protein (GFP), expression of which, confers a recognizible physical characteristic to transformed cells, the chloramphenicol transferase gene, expression of which, detoxifies chloramphenicol.

The selectable marker could be inserted between a promoter and a terminator in an expression cassette. Said expression cassette being integrated in the same vector as the expression cassette containing the puroindoline gene.

According to a particularly preferred method of the invention, the promoter is the rice actin promoter, for the expression cassette containing the bar gene.

According to a preferred method of the invention, the terminator is the Nos terminator, for the expression cassette containing the bar gene.

Advantageously, the expression cassette containing the selectable marker is comprised between two Ds elements (transposons) in order to be removed at the later stage by interacting with the Ac transposase. This elimination system is described in Yoder et al. (1993).

In preparing the expression cassettes, the various DNA fragments may be manipulated, so as to provide DNA sequences in the proper orientation and, as appropriate, in the proper reading frame. Towards this end, adapters or linkers may be employed to join the DNA fragments and/or other manipulations may be required to provide convenient restriction sites, removal of superfluous DNA, removal of restriction sites, or the like. For this purpose, in vitro mutagenesis, primer repair, restriction, annealing, ligation, PCR, or the like may be employed, where nucleotide insertions, deletions or substitutions, for example transitions and transversions, may be involved. These techniques are well known by those skilled in the art.

Transformation:

A transgenic maize plant may be generated by transformation with at least an expression cassette mentioned above, so that puroindoline is expressed in the transgenic maize.

The DNA construct which allows the expression of a puroindoline-a and/or puroindoline-b protein is introduced into a plant cell, a plant tissue, or a plant. Where the transformed maize is to express puroindoline-a and puroindoline-b, both transgenes can be introduced in plant cells by means of either a unique DNA construct or by two DNA constructs. Alternatively a plant expressing puroindoline-a can be crossed with a plant expressing puroindoline-b.

The transformation of plants may be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press, incorporated herein by reference.

As used herein, the term "transformation" encompasses the genetic manipulation of the plant, cell, cell line, callus, tissue, plant part, and the like. That is, such cell, cell line, tissue, plant part, or plant which has been altered by the presence of recombinant DNA wherein said DNA is introduced into the genetic material within the cell, either chromosomally, or extra-chromosomally. Recombinant DNA includes foreign DNA, heterologous DNA, and chimeric DNA. The recombinant DNA can be random either targeted in a specific locus by homologous recombination according to techniques already known by the one skilled in the art.

The foreign nucleic acid may be mechanically transferred by microinjection directly into plant cells (cytoplasm or nucleus) by use of micropipettes. Alternatively, the foreign nucleic acid may be transferred into the plant cell by using polyethylene glycol in presence of bivalent cations ($Ca^{2+}$). This forms a precipitation complex with the genetic material that is taken up by the cell. (Paszkowski et al., 1984).

The introduced gene may also be introduced into the plant cells by electroporation. (Fromm et al., 1985, which is incorporated herein by reference). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) may also be used as a vector for introducing the foreign nucleic acid into plant cells. (Hohn et al., 1982; Howell, U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of transformation is particle bombardment (WO 98/49316). The bombardment is realized with particles coated with the plasmid DNA of interest, using a particle gun (M. Fromm et al., 1980). The transformation could be carried out according to the method described by Finer et al. (1992), using a tungsten or gold particle gun.

Another method of introduction of nucleic acid segments into plant cells is to infect a plant cell, an explant, a meristem or a seed with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome. (Horsch et al., 1984; Fraley et al., 1983).

Further maize tissues that are capable of transformation according to the methods described herein include calli, cell suspension cultures, anthers, microspores, embryos, inflorescences, and the like. Cell suspension cultures can be derived from calli of embryos, leaf tissues, young inflorescences, anthers, etc.

Callus can be originated from any tissues of maize plants. Preferably the tissue utilized in initiating callus is immature tissue such as immature embryos, immature inflorescences, and the basal portion of young leaves.

Alternatively, callus can be originated from anthers, microspores, mature embryos and in principle any other tissue of maize capable of forming callus and or secondary embryos.

An especially useful tissue for producing regenerable callus is the scutellum of immature maize embryos.

A preferred method of introducing the nucleic acid segments into plant cells is transformation by *Agrobacterium tumefaciens*.

After transformation of the plant cells or plant, those plant cells or plant transformed so that the desired DNA segment is integrated can be selected by an appropriate selectable marker.

Selection:

Selection of transgenotes for further study is typically based upon a medium selection. The term "transgenote" refers to the immediate product of the transformation process and to resultant whole transgenic plants.

The engineered maize plant material may be selected or screened for transformants (those that have incorporated or integrated the introduced gene construct(s)). An isolated transformant may then be regenerated into a plant Alternatively, the engineered plant material may be regenerated into a plant or plantlet before subjecting the derived plant or plantlet to selection or screening for the marker gene traits.

Procedures for regenerating plants from plant cells, tissues or organs, either before or after selecting or screening for marker gene(s), are known to those skilled in the art.

A transformed maize plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the beta-glucuronidase, luciferase, B or C1 genes) that may be present on the recombinant nucleic acid constructs of the present invention. Such selection and screening methodologies are well known to those skilled in the art.

Medium comprising glufosinate-ammonium is the preferred medium for the selection step involved in growing transformed plant cells or tissues, preferably immature embryos (when the bar gene is used as selectable marker).

After growth on selection medium the transformed and selected tissue is allowed to grow.

For plants surviving selection on glufosinate-ammonium containing medium, genomic DNA is extracted and probed to confirm transformation. Methods are available in the art for the isolation of DNA from biological material in culture as well as for confirming the presence of DNA of interest. Such methods to confirm include but are not limited to 1) PCR analysis as well as Southern blot hybridisation for determining the structure of the recombinant DNA insert. See, Southern, EM (1975) Journal of Molecular Biology 98 :503 and Mullis, KB (1987) Methods in Enzymology 155 :335;
2) Northern blot, reverse transcriptase-PCR amplification for detecting and examining RNA transcripts of the gene construct;
3) Protein gel electrophoresis, Western blot techniques, immunoprecipitation, or enzyme-linked immunoassays, where the gene construct products are proteins.

Protein Expression:

The puroindoline expression is analysed by Enzyme-Linked-Immunoabsorbant-Assay (ELISA known by the one skilled in the art) in transgenic plants.

Regeneration:

Normally, regeneration is involved in obtaining a whole plant from the transformation process. The term "regeneration" as used herein, means growing a whole plant cell, a group of plant cells, a plant part or a plant piece (for example, from a protoplast, callus, or tissue part).

Methods of regenerating whole plants from plant cells are known in the art, and the method of obtaining transformed and regenerated plants is not critical to this invention.

In general, transformed plant cells are cultured in an appropriate medium, which may contain selective agents such as antibiotics, where selectable markers are used to facilitate identification, of transformed plant cells. Once callus forms, shoot formation can be encouraged by employing appropriate plant hormones in accordance with known methods and shoots transferred to rooting medium for regeneration of plants. The plants may then be used to establish repetitive generations, either from seeds or using vegetative propagation techniques.

Thus, the invention also relates to maize plant tissue, plants or seeds containing the nucleic acid sequences described above. In the context of the disclosure "plant tissue" refers to any tissue of a plant, in planta, or in culture. This term includes, but is not limited to, whole plants, plant cells, plant organs, plant seeds, protoplasts, callus, cell cultures and any groups of plant cells organized into structural and/or functional units. The use of this term in conjunction with, or in the absence of, any specific type of plant tissue as listed above or otherwise embraced by this definition is not limited to be exclusive of any other type of plant tissue.

The cells which have been transformed may be grown into plants in accordance with conventional techniques. See for example, McCormick et al. (1986). These plants may then be grown, and either pollinated with the same transformed strain or different strains, and the resulting hybrid having the desired phenotypic characteristic identified. Two or more generations may be grown to ensure that the introduced phenotypic characteristic is stably maintained and inherited and then seeds harvested to ensure the desired phenotype or other property has been achieved.

Improved embryogenic cultures of maize can be obtained by using previously regenerated material as a source of starting material. The starting material for these improved cultures may be either immature embryos obtained directly from regenerated plants, or the starting material may be seeds from regenerated plants grown as source of immature embryos.

Vectors:

The decision as to whether to use a vector, or which vector to use, is guided by the method of transformation selected, and by the host cell selected.

Where a naked nucleic acid introduction method is used, then the vector need be no more than the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, KB (1987), *Methods in Enzymology*).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenotes.

The vector can exist, for example, in the form of a phage, a plasmid or a cosmid. The construction of such expression vectors for transformation is well known in the art and uses standard techniques. Mention may be made of the methods described by Sambrook et al. (1989).

In a preferred method, the expression cassette comprising the puroindoline gene, and the expression cassette comprising the marker gene are inserted into the same vector.

Host Cells:

The decision as to whether to use a host cell, or which host cell to use, is guided by the method of transformation.

In a particular embodiment, the present invention provides a host cell comprising a vector as described above. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

Method of Enhancing Corn Starch Extractability

The invention thus provides a method for improving corn starch extractability. In the context of the invention starch extractability is more particularly carried out by a wet milling process. A wet milling typically comprises five basic steps consisting of:

cleaning;
steeping;
germ separation;
grinding and screening; and
starch separation.

In the above process, faster hydration and easier starch protein separation of corn is achieved by using corn with increased grain softness, such as obtainable by expression of a grain softness-enhancing gene, for instance a puroindoline gene.

The invention thus relates to the use of a maize that is transformed so as to express a grain softness-enhancing gene, as a source of corn with improved starch extractability.

The invention further provides a method of obtaining corn with improved starch extractability comprising cultivating a maize transformed with a grain softness-enhancing gene and harvesting corn produced by said maize.

Additionally, the invention relates to a method of improving starch extractability comprising cultivating a maize transformed with a grain softness-enhancing gene and harvesting corn produced by said maize A method of obtaining such a transformed maize is thoroughly described in the above section "Production of maize with increased grain softness" for the one skilled in the art to carry out the invention.

Preferably, said grain softness-enhancing gene is puroindoline-a or puroindoline-b gene. In particular, said transformed maize may be transformed with and express puroindoline-a and puroindoline-b.

Accordingly, a maize transformed with a grain softness-enhancing gene may for instance be obtained by introducing a nucleic acid sequence which encodes a puroindoline protein into at least a maize cell and cultivating such transformed cell in conditions for regenerating fertile stable transformed maize plant.

In another embodiment, the invention relates to maize plants transformed with a grain softness-enhancing gene, in particular with a puroindoline gene. These maize plants and grains may be transformed either with a puroindoline-a gene, a puroindoline-b gene or both of them.

The invention further provides maize plants and maize grains with an improved oil content, i.e. with an increased oil content compared with the corresponding non-transformed, wild-type, maize plants or grains.

In another embodiment, the Invention proposes an improved process of extracting corn starch, comprising wet milling a corn with increased grain softness to provide highly pure corn starch. In particular, the improved process comprises wet milling a corn that has been transformed so as to express a grain softness-enhancing gene to provide corn starch.

Said corn with increased grain softness may be produced by a maize transformed with a grain softness-enhancing gene. Thus, preferably said maize and corn express a puroindoline protein.

The improvement in the wet milling process comprises increasing starch yield through in a given time frame, as compared to wet milling of a corn from a wild-type maize that does not express a grain softness-enhancing gene. Such an improvement more particularly relies on a reduction of the steeping time and/or on a reduction of the number of washes in the starch separation step.

Preferably, in the process of the invention, the overall time necessary to achieve a starch extraction yield of at least a 95% is below 30 hours. Still preferably, the overall time necessary to achieve a starch extraction yield of at least a 95% is below 27 hours, more preferably below 24 hours.

Advantageously, the number of washes in the starch separation step is dramatically reduced, of at least 50% (two-fold), as compared to wet milling of corn without increased softness. Preferably, the number of washes in the starch separation step is between 2 to 4.

Advantageously, the steeping step time of the process of the invention is reduced by at least 10%, preferably at least 20%, preferably by at least 30%, as compared to wet milling of corn without increased grain softness. Preferably the steeping step time is below 24 hours.

Preferably, the starch produced by the process of the invention is highly pure, that is with a degree of purity over 99%, and still preferably over 99.5 percent pure.

The present invention will be further understood in view of the annexed figures and following examples.

EXAMPLES

By way of example, and not limiting, a preferred embodiment of the present invention entails introducing a full-length puroindoline-a or -b coding sequence in sense orientation into maize immature embryos. These transgenotes are grown into plants and variations in grain hardness and in starch extractability are observed.

Example 1

DNA Constructs

The restriction enzymes used for cloning are provided by New England Biolabs (New England Biolabs, UK). The enzymatic reactions are carried out by following the protocols described by Sambrook et al., in the manual: Molecular cloning (Molecular cloning: A Laboratory Manual, 1989, Cold spring Harbor Laboratory Press, Cold Spring Harbor, N.Y.).

The promoter of the high molecular weight glutenin (HMWG) gene 1Dx5 (Halford et al., 1989) was isolated from wheat genomic deoxyribonucleotidic acid (DNA) using PCR. Primers carried ClaI and EcoRI sites. The HMWG promoter was digested with ClaI-EcoRI and ligated Into the ClaI-EcoRI site of pBluescript (Stratagene).

The Nos terminator (Depicker et al., 1992) was isolated as a PCR fragment and ligated into the BamHI-SacI site of this subclone to make pDV03000 (WO 00/31274).

The cDNA sequences pTa31 and pTa19B2 (Gautier et al., 1994) encoding precursors of puroindoline-a and puroindoline-b respectively having cleavable N-terminal and C-terminal sequences putatively involved in targeting, were introduced between the HMWG promoter and the Nos terminator of pDV03000 as follows.

The cDNA clones were digested with NotI and SalI and the ends made blunt. The blunt-ended pTa31 and pTA19B2 were ligated into the SmaI site of pDV03000 to give pPIA and pPIB, respectively.

The sequence TCGACCCACGCGTCCG (SEQ ID N°5) was introduced between the SmaI site and the beginning of the puroindoline-a or the puroindoline-b cDNA sequences. Using this cloning strategy no ATG was introduced between the HMWG promoter and the ATG of puroindoline-a or the puroindoline-b sequences.

The sequence GCGGCC was introduced at the end of the puroindoline-a or the puroindoline-b CDNA sequences between the poly (A) tail and the Sma1 site.

The puroindoline-a expression cassette, PIA, containing the HMWG promoter, the puroindoline-a gene, and the Nos terminator, was removed from pPIA within a fragment of approximately 1.4 kb using a NotI-XhoI digest. The reaction was started with a NotI digestion, followed by a blunting reaction with T4 DNA polymerase and completed with a XhoI digestion.

The puroindoline-b expression cassette, PIB, containing the HMWG promoter, the puroindoline-b gene, and the Nos terminator was removed from pPIB within a fragment of approximately 1.4 kb in the same way as for the puroindoline-a expression cassette.

Figure 2:
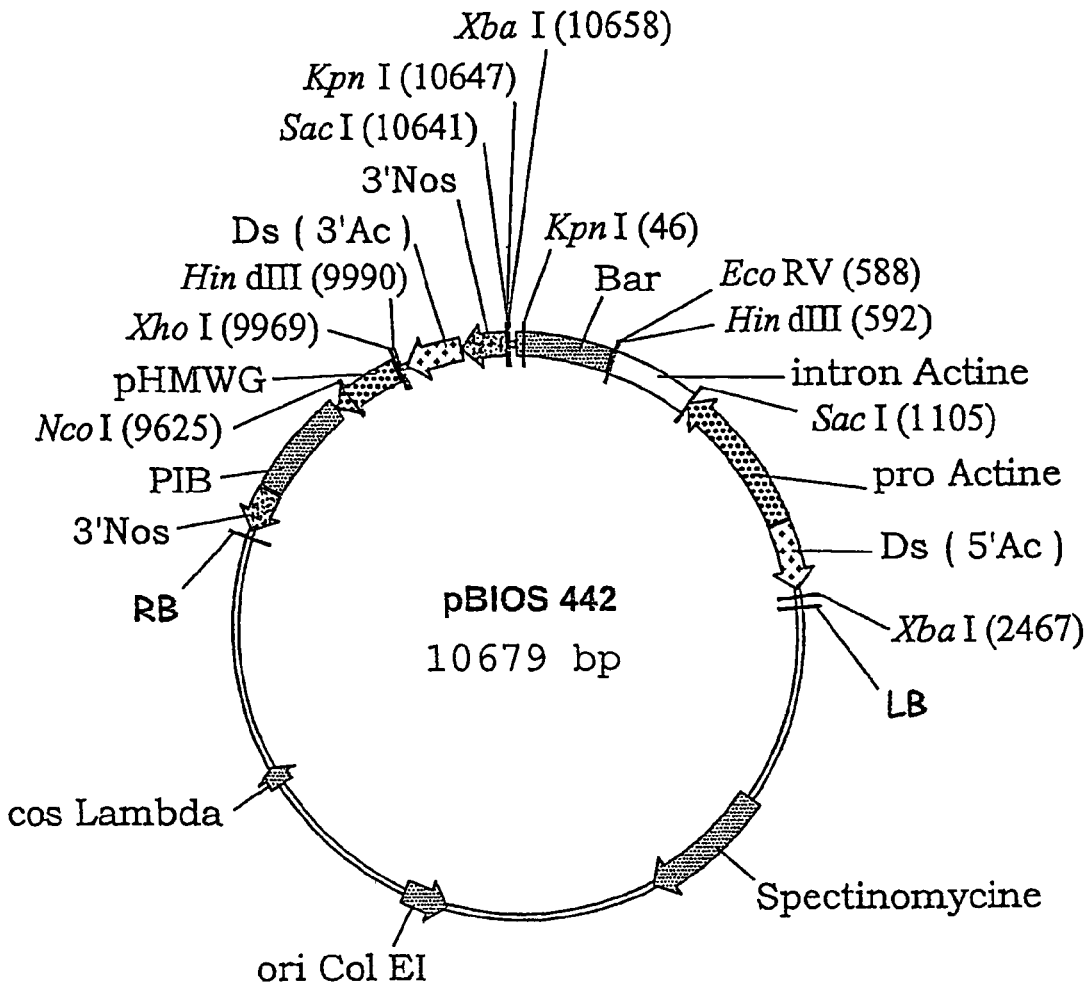
FIG. 2 represents plasmid pBIOS 442 which contains the puroindoline-b cassette.

The puroindoline-a or the puroindoline-b expression cassette (NotI/blunt-XhoI fragment) were introduced into the super-binary maize transformation vector pBIOS 342 opened with PmeI and XhoI. This resulted in plasmids pBIOS 443 (containing the puroindoline-a cassette, FIG. 1) and pBIOS 442 (containing the puroindoline-b cassette, FIG. 2) respectively.

The maize super-binary transformation vector pBIOS 342 carries an expression cassette containing the following elements: Ds element-rice actin I promoter-rice actin I first intron-Bar gene-Nos terminator-Ds element. It was obtained by exchanging the NsiI fragment containing part of the rice actin I first intron, the NptII gene and part of the Nos terminator from pBIOS 340 with the NsiI fragment from pDM302 (Cao et al., 1992) containing part of the rice actin I first intron, the bar gene and part of the Nos terminator.

pDM302 was prepared as follows:

The coding region of the bar gene from *Streptomyces hygroscopicus* that encodes the PAT (Phosphinothricine Acetyl Transferase) activity was removed from plasmid pIJ4104 (White et al., 1990) by the restriction enzyme SmaI (600 bp fragment) and cloned into the expression vector pCOR113 (McElroy et al., 1991) after the 5' fragment (promoter and first intron) of rice Actine 1 gene (Act-1). The 4.9 kb plasmide pDM301 containing the expression cassette Act1-bar was thus obtained. The expression cassette Act1-bar of pDM301 was removed within a 2.0 kb XhoI-XbaI restriction fragment and cloned between the SalI and XbaI sites, upstream the terminator sequence of the nos gene that encodes nopaline synthase (plasmid pNOS72). The 4.7 kb plasmid pDM302 so obtained contained the expression cassette Act1-bar-nos.

Plasmid pBIOS 340 is a super-binary transformation vector containing the NptiII gene under control of the rice actin I promoter and its first intron and the Nos terminator between 2 Ds elements (Yoder et al., 1993). It has been generated by introducing the XbaI-XhoI fragment (Ds element-rice actin I promoter and its first intron-NptiII gene-Nos terminator-Ds element) from pBIOS 339 into the super-binary transformation vector pBIOS 273 opened with XbaI and XhoI. Plasmid pBIOS 339 is a pUC derived plasmid containing the NptiII gene under control of the rice actin I promoter and its first intron and the Nos terminator between 2 Ds elements.

Figure 3:
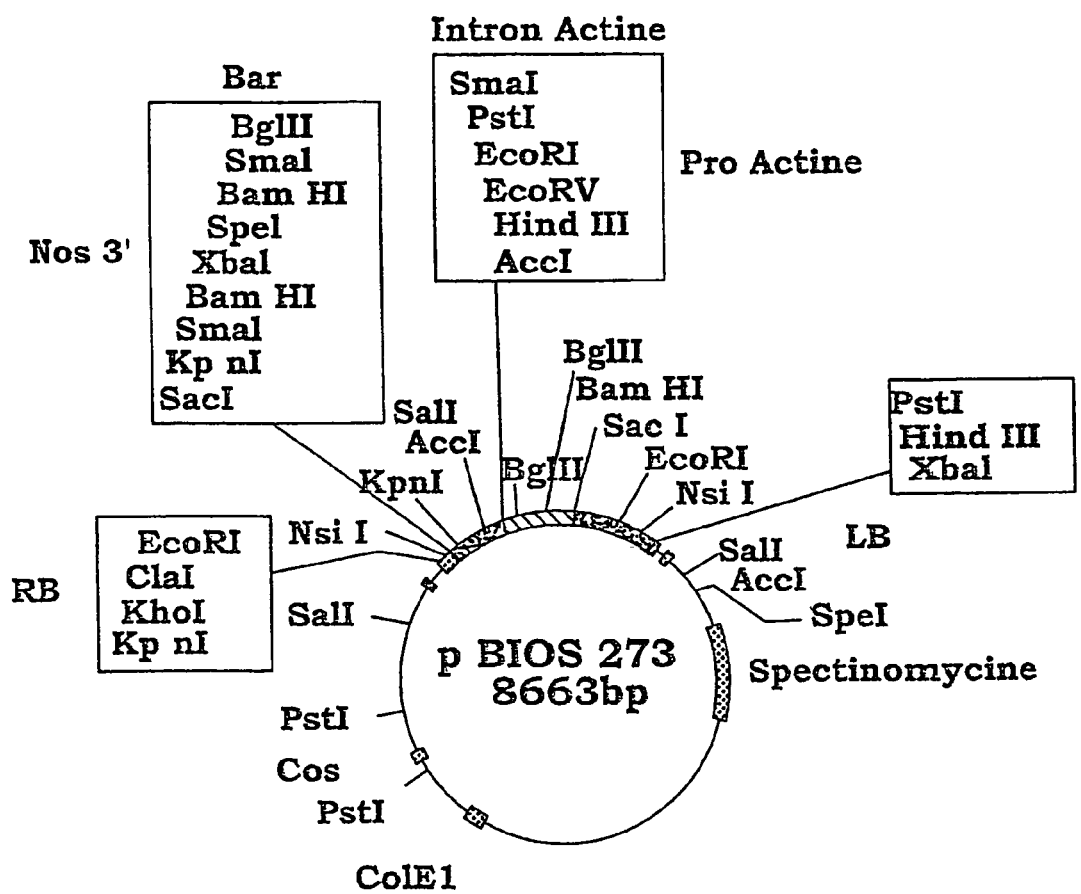
FIG. 3 represents plasmid pBIOS 273 which contains an expression cassette including the rice actin promoter, bar gene and 3' Nos terminator.
Figure 4:
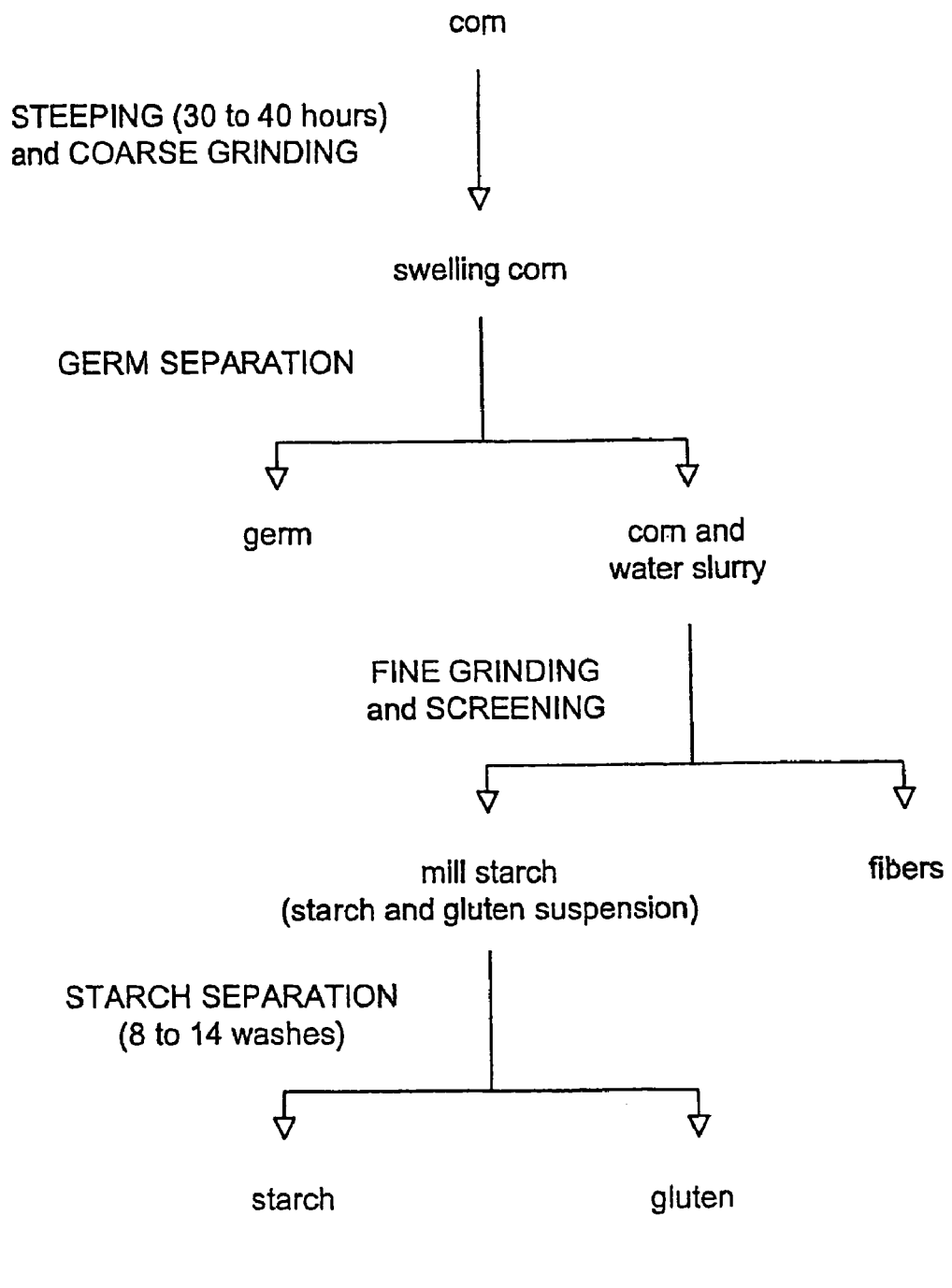
FIG. 4 shows a schematic process for starch separation.

Plasmid pBIOS 273 (FIG. 3) carries an expression cassette including rice actin promoter, bar gene, and 3'Nos terminator. This plasmid has been built according to standard molecular biology techniques well known from the skilled person.

Plasmid pBIOS 273 is in the form of a donor vector derived from vector pSB12 (EP 672 752), of about 8.6 kb, comprising:

ori origin: origin of a plasmid replication Col E1, necessary for the maintenance and multiplication of the plasmid in the bacteria, a gene that provides resistance to spectinomycin, and that is expressed only in bacteria, a T-DNA that comprises the bar gene providing resistance to Basta® herbicide under the control of rice actin promoter and 3'Nos terminator.

Plasmid pBIOS 273 has been produced in two steps:

cloning fragment BspDI/XhoI (actin promoter-bar gene-Nos terminator) of vector pDM 302 (Cao et al., 1992) into SmaI and BspDI sites of vector pSB12 (EP 672 752). The vector resulting from the cloning is called pBIOS 272.

deletion XhoI site in position 3363 of vector pBIOS 272 by partial digestion with XhoI and action of DNA Polymerase I, large (Klenow) fragment The vector obtained, that possesses a unique XhoI site, is called pBIOS 273.

The actin promoter corresponds to the non coding 5' region of actin 1 gene in rice and its first intron (Mc Elroy et al., 1991; Gene Bank n°S 44221).

3'Nos terminator is a terminator of nopaline synthase that corresponds to non coding 3' region of the nopaline synthase in plasmid Ti *Agrobacterium tumefaciens* nopaline strain (Depicker et al., 1982).

NptiII gene has been isolated from transposon Tn5 of *Eschedichia coli* (Berg et al., 1983). This gene encodes neomycin phosphotransferase type II enzyme that catalyses O-phosphorylation of aminoglycoside antibiotics such as neomycin, kanamycin, gentamycin and G418 (Davies and Smith, 1978). This gene provides resistance to kanamycin, that is used as a selection agent in plant genetic transformation. It is described by Bevan et al. (Genbank n° U00004).

Example 2

Maize Transformation Method and Selection Procedure

Any transformation method (electroporation, biolistics, microfibres, particle gun, *Agrobacterium* . . . ) may be used.

Preferentially, the transformation of maize is performed by using the *Agrobacterium tumefaciens* technique as described by Ishida et al., 1996.

Immature embryos are cocultured with *Agrobacterium tumefaciens* strain LBA 4404 containing the super-binary vector, including the bar gene as selectable marker gene. The induced embryogenic calli are grown on media containing phosphinotricin for selection of the transformed ones.

Plantets are then regenerated from these calli by modifying the hormonal balance in the presence of phosphinotricin. These plants are then acclimatized In a greenhouse, where they can be crossed or selfpollinated.

2.1—Production of the Super-binary Vectors 2.1.1—Production of the Super-binary Vector pREC 443

The super-binary vector used to transform the maize was derived from homologous recombination between two vectors: the vector pBIOS 443 and the Japan Tobacco vector pSB1 (EP 672 752). The vector pBIOS 443, constructed as previously (Example 1), comprises, firstly, the T-DNA containing the expression cassette for the puroindoline-a gene, inserted between the pHMWG promoter and the Nos terminator, and the expression cassette for the selectable gene, the Bar gene (Ds element-rice actin I promoter-rice actin I first intron-Bar gene-Nos terminator-Ds element). In addition, pBIOS 443 also contains the gene for resistance to spectinomycin and the origin of replication in *E. coli*. The vector pSB1 contains the virB, virC and virG genes of the plasmid pTiBo542 present in the supervirulent *Agrobacteirum* strain A281 (ATCC 37349), the gene for resistance to tetracycline, and an origin of replication which is functional in *E. coli* and *Agrobacterium*. The vectors pSB1 and pBIOS 443 possess a homologous region which allows them to recombine and generate the super-binary vector pREC 443.

Homologous recombination between the two vectors takes place in *Agrobacterium*. The vector pBIOS 443 was introduced into *Agrobacterium* strain LBA 4404 (Hoekema et al., 1983) containing the vector pSB1 by electroporation using a CELL PORATOR Voltage Booster device (GIBCO BRL) according to the method described by Mattanovitch et al. (1989) and the protocol given by the supplier (Life technologies, USA).

The agrobacteria containing the super-binary vector pREC 443 were selected on LB medium in the presence of rifampicin and spectinomycin. The gene for resistance to rifampicin is carried by the bacterial chromosome. The resistance to spectinomycin, carried by the vector pBIOS 443 (origin of replication functional in *E. coli*), may only be expressed after homologous recombination with the vector pSB1 (origin of replication functional in *Agrobacterium* and *E. coli*).

The super-binary vector pREC 443 possesses the T-DNA which contains the expression cassettes for the Bar gene and for the puroindoline-a gene, origins of replication which are functional both in *E. coli* and *Agrobacterium*, the genes for resistance to tetracycline and to spectinomycin, and the virB, virC and virG virulence genes of the plasmid pTIBo542.

2.1.2—Production of the Super-binary Vector PREC 442

The same protocol as described above (example 2.1.1) was used to produce the super-binary vector pREC 442. This super-binary vector was derived from homologous recombination between two vectors: the vector pBIOS 442 (comprising the expression cassettes for the puroindoline-b gene and for the selectable Bar gene) and the vector pSB1.

2.2—Method for Transformation and Regeneration of Maize

The maize transformation methods are known by those skilled in the art and the method presented hereafter is not limitating.

2.2.1—Method for Transformation of Maize with pREC 443 and Regeneration of the Transformed Plants Immature embryos taken 10+/−2 days after fertilization (size ranging from 1 to 1.2 mm) were cocultured with *A. tumefaciens* strain LBA 4404, containing the super-binary vector pREC 443, for at least 5 minutes, and then placed on LSA medium for 5 days in the dark and at 25° C.

The transfer followed by the expression of the genes (selectable gene and gene of interest) in maize is based on the natural properties of *Agrobacterium tumefaciens* (Zambrisky et al., 1989) and on the strategy of the super-binary vector (Hiei et al., 1994 and Ishida et al., 1996). All the media used are described in Ishida et al, 1996.

Firstly selection was applied to the transformed calli: the embryogenic calli were transferred onto LSD5 medium containing phosphinothricin at 5 mg/l and cefotaxime at 250 mg/l (elimination or limitation of contamination with *Agrobacterium tumefaciens*). This step was carried out for two weeks in the dark and at 25° C. The second selection step was carried out by transferring the embryos which developed on LSD5 medium onto LSD10 medium (phosphinothricin at 10 mg/l) in the presence of cefotaxime, for 3 weeks under the same conditions as previously. The third selection step consisted of excising the type I calli (fragments of 1 to 2 mm) and transferring them, for 3 weeks in the dark and at 25° C., onto LSD10 medium in the presence of cefotaxime.

The plantlets were regenerated by excising the type I calli which have proliferated and transferring them onto LSZ2 medium in the presence of phosphinothricin at 5 mg/l and cefotaxime, for 2 weeks at 27° C. under light (16 hours daylength). The type I calli having proliferated were then placed onto a RM+GC100 medium containing 2 mg/l phosphinothricin and 100 mg/l cefotaxime at 27° C. for 2 to 4 weeks under light (16 hours daylength).

The plantlets which regenerated were transferred onto T1G2 medium containing 2 mg/l phosphinothricin for 1 to 2 weeks at 27° C. under light (16 hours daylength) for the development step. The plants obtained were then transferred to a phytotron in order to allow them to acclimatise.

The *Streptomyces hygroscopicus* Bar gene encodes a phosphinotricin acetyltransferase (PAT) which inactivates phosphinotricin—active molecule of the herbicide. Basta®—by acetylation. The cells carrying this gene are therefore made resistant to this herbicide and can be selected by it. So the descendants of the calli and the plants which have the T-DNA which contains the puroindoline-a gene and the Bar gene integrated into their genome can be followed by virtue of the herbicide resistance.

In order to identify the plantlets resistant to the herbicide (glufosinate-ammonium), due to integration of the transgene, a selection step was effected with a Liberty® F1 solution (AgrEvo France). At the 4- to 5-leaf stage, 8 to 10 days after germination, the Liberty® test was carried out. The solution was applied by leaf painting on the second or third leaf. The glufosinate-ammonium solution was used at 0,75 g/l. The Liberty® test was scored 5 days later: the necrotic leaves revealed the plants which have not been transformed. The non-resistant (sensitive) plants presented a necrosis of the treated area. The resistant plants did not present necrosis 5 days after herbicide treatment.

The plants are then grown in a greenhouse where they may be crossed or self-fertilized.

44 plants transformed with puroindoline-a gene have been obtained.

2.2.2—Method for Transformation of Maize with pREC 442 and Regeneration of the Transformed Plants The maize transformation method with pREC 442 was the same as the one described with pREC 443 in example 2.2.1.

85 plants transformed with puroindoline-b gene have been obtained.

Example 3

Molecular Characterisation of the Transformants

Among the transformants, those which exhibit a single locus/single copy insertion (1 copy of the gene of interest and one copy of the selectable gene) without any undesirable plasmid sequence are preferentially chosen. The Southern technique, with several suitable restriction enzymes and several suitable probes (Southern, 1975), can in particular be used to identify and characterize the insertion into the genome of the plant, thus making it possible to differentiate the transformation events. This methodology in fact makes it possible to demonstrate individual differences in the size of the restriction fragments obtained with a given enzyme and a given probe, corresponding to defined positions on the genome.

Genomic DNA extraction was performed with the Qiagen extraction kit (Qiagen Dneasy Plant Mini Kit) according to the manufacturer with a slight modification: the DNA elution buffer is diluted 10× with water and elution is done with 200 μl instead of the 150 μl specified by the manufacturer. The DNA is then precipitated and resuspended in 15 μl water.

Southern blotting is then performed to show the insertion of the transgene into the genome of the plant, and to evaluate the number of copies and to characterize the integration pattern.

The DNA obtained was digested with EcoRV restriction enzyme, fractionated on a 0.8% agarose gel by electrophoresis and transferred on a Hybond N+ membrane (Amersham), and finally hybridised with probes.

The different probes are obtained either by restriction digestion of a plasmid containing a fragment of the corresponding probe or after PCR amplification of the corresponding fragment. Extraction and gel purification of the restricted or amplified fragment is realised using the Qiaquick Gel extraction Kit (Qiagen). The extracted fragment is then labelled with the Amersham Megaprime DNA labelling system, accordingly to the manufacturer's protocole.

The following strategy was used:

EcoRV restriction of the extracted plant genomic DNA.

HMWG promoter probe: used to detect the insertion of the puroindoline-a or -b expression cassette and the Bar gene.

actin first intron probe: used to detect the presence of the promoter driving the expression of the Bar gene.(actin promoter).

Extra-Border probes: used to detect the presence of plasmid sequences other than the T-DNA.

Estimation of the complexity of the inserted T-DNA (one locus or several loci, one or several copies within a locus) is given by the number of hybridising fragments with the different probes and the size of those fragments.

The profiles obtained were those expected.

Other strategies could be used (other restriction enzymes and other probes).

In this way 15 puroindoline A and 20 puroindoline B lines were identified with single or low number of insertions for further multiplication and study.

TABLE 1

Selected Puroindoline A lines

| Lab code | Glasshouse code | Field code |
|---|---|---|
| 01808.01 | 163.001.4 | BW01 |
| 01799.01 | 165.001.2 | BW02 |
| 01777.01 | 166.001.1 | BW03 |
| 01824.01 | 174.001.1 | BW04 |
| 01846.01 | 174.006.1 | BW05 |
| 01837.01 | 174.008.1 | BW06 |
| 01920.01 | 177.001.1 | BW07 |
| 01859.01 | 177.002.2 | BW08 |
| 01905.01 | 188.001.2 | BW09 |
| 01912.01 | 188.002.1 | BW10 |
| 01906.02 | 188.003.1 | BW11 |
| 01907.03 | 188.004.1 | BW12 |
| 01961.02 | 201.005.1 | BW13 |
| 01831.01 | 174.004.1 | BW14 |
| 01793.02 | 165.001.1 | BW15 |

TABLE 2

Selected Puroindoline B lines

| Field code | Glasshouse code | Lab code |
|---|---|---|
| BU01 | 01842.01 | 173.004.3 |
| BU02 | 01865.01 | 182.001.1 |
| BU03 | 01867.01 | 183.002.1 |
| BU04 | 01909.03 | 183.021.1 |
| BU05 | 01921.01 | 183.008.3 |
| BU06 | 01879.01 | 184.002.2 |
| BU07 | 01880.02 | 184.003.1 |
| BU08 | 01922.01 | 184.005.1 |
| BU09 | 01883.01 | 187.009.1 |
| BU10 | 01901.02 | 187.011.1 |
| BU11 | 01924.01 | 187.015.1 |
| BU12 | 01925.01 | 187.016.2 |
| BU13 | 01926.02 | 187.017.1 |
| BU14 | 01934.02 | 187.019.1 |
| BU15 | 01886.01 | 192.001.2 |
| BU16 | 01928.01 | 192.004.1 |
| BU17 | 01929.01 | 193.001.1 |
| BU18 | 01939.01 | 193.003.2 |
| BU19 | 01958.01 | 199.009.1 |
| BU20 | 01967.01 | 204.003.1 |

Example 4

Hardness Determination

The effect of the puroindoline gene on seed texture was assessed in two ways.

4.1—Particle Size Index

The principle is that the kernels are ground into flour and the distribution of the particle sizes in the resultant flour is determined. The size of the particles is indicative of ease of separation of the starchy endosperm into component parts where large particles are correlated with difficult separation and small particles correlated with easier separation.

A sample of grain was milled during 1 minute (IKA grinder). The flour was passed through a 250 μm sieve. The weight of partides in each size fraction was measured. The hardness (weight of the fraction above 250 μm/total weight) was expressed in percentage.

4.2—Rapid Viscosity Analysis

The kernels were ground with an IKA mill and then defatted (10 minutes in diethylether at 100° C. with a Soxtec machine, (Foss Tecator); then samples are dried at room temperature overnight). 2.5 g of sample were added to 25 ml of deionised water and placed in the stirchamber of the Rapid Visco Analyser (RVA Newport).

The analysis was done with the standard 1 profile with an RVA 3D+.

The temperature profile was: start temperature, 50° C. with cooking to 95° C. at a rate of 12° C./min. The mix was left to stand at 95° C. for 2 minutes and 30 seconds, and then cooled to 50° C. The total analysis took 13 minutes.

The following parameters were noted for each sample and compared:

Pasting temperature

Peak viscosity (Rapid Viscometer Unit, RVU)

Breakdown (viscosity at the peak–viscosity at the end of standing time at 95° C., RVU)

Set back (final viscosity–viscosity at the end of standing time, RVU)

Final viscosity (RVU)

The peak viscosity (of the defatted sample) is inversely proportional to the hardness.

4.3—Results

TABLE 3

| Sample Code | Hardness (%) | Breakdown RVA) defatted | Peak viscosity (RVA defatted) (RVU) | Set Back (RVA defatted) | Pasting temperature (RVA defatted) (° C.) | Final Viscosity (RVA defatted) (RVU) |
|---|---|---|---|---|---|---|
| BU– (control maize) | 73 | 1 | 44 | 32 | 81.5 | 75 |
| BU+ (maize transformed with puroindoline-b gene) | 63 | 3 | 53 | 34 | 78.3 | 83 |

Maize lines transformed with the puroindoline-b gene were found to be softer than the non-transgenic ones. The viscosity analysis confirmed this result.

Example 5

Starch Extractability Determination

On the basis of preferably monocopy insertions, 15 puroindoline A and 20 puroindoline B lines were selected for further analysis. The original regenerants (T0) were crossed with A188 line to produce the T1 generation. The T1 was further multiplied by selfing to produce the T2 generation. The introduced puroindoline gene was segregating in the T2 generation, 3:1 transgenic: null-type. The T2 kernels have two phenotypes "opaque" and "translucent". The "opaque" appearance is correlated with the presence of the puroindoline gene.

The kernels from the 15 puroindoline A lines were divided into two batches BW:Opaque and BW:Translucent. The kernels from the 20 puroindoline B lines were similarly divided into two batches BU:Opaque and BU:Translucent.

In this way it was possible to determine starch extractability on early generation material that was still segregating. This way is not a limitation, other ways could be used.

100 g of kernels from each batch was used to determine starch extractability in a wet-milling procedure.

Sample Preparation:

Eight 100-g samples (two each of Sample Identities BU+ and BW+, transgenic plants; and BU− and BW−, non-transgenic controls) were wet milled to compare the wet-milling characteristics of selected transgenic plants versus that of non-transgenic controls using the conventional 40-hour batch steep and a shortened 24-hour steeping process. The shortened 24-hour batch steeping process was performed first on each of the four samples in the following randomly selected order BU−, BW−, BW+ and BU+. The conventional 40-hour batch steeping process was then performed on the four replicate samples in reverse order BU+, BW+, BW− and BU−. All equipment was thoroughly washed and rinsed with a 100-ppm hydrogen peroxide solution between samples to prevent sampling contamination.

Steeping:

Each sample was steeped in a 300-ml solution containing 0.2% $SO_2$ (2000 ppm) and 0.5% lactic acid (5000 ppm) that is placed in a pre-heated water bath set at 50° C. for the sample's designated steeping time (either the conventional 40-hour steep time or the shortened 24-hour steep time). After steeping, the steep water was drained and analyzed for total solids. Total solids in steep water was determined by drying the entire sample in a large-capacity forced-air oven set at 50° C. for 24 hr followed by drying in a convection oven at 130° C. for 3 hr (AOAC 1992, method 14.004).

Coarse Grinding:

The steeped corn was ground with 200-ml water in a 1-L Waring blender equipped with blunted blades and set at 60% speed for 4 minutes. The coarsely ground slurry was then strained through a 7-mesh sieve (pore size=2.8 mm) placed atop a 4-L Waring blender canister. If any whole kernels remained after initial grinding, they were recycled and ground once again with an equal weight of water. Any recycled grinds were then added to the previously ground sample and strained.

Germ/Coarse Fiber Separation:

After straining, the germ/coarse fiber fraction within the 7-mesh sieve was placed in a 10-L bucket containing 800-ml water. The bucket was then sealed and placed in sieve shaker set at 50% speed for 5 minutes. The sieve was removed from the bucket and the washed germ/coarse fiber fraction was then dried in the sieve for 24 hours in a large-capacity forced air oven set at 50° C. After drying, the sample was aspirated at an air pressure of 550 mm Hg to separate germ meal from coarse fiber. The remaining slurry from the 10-L bucket was combined with the slurry in the 4-L blender canister.

Fine Grinding:

The degermed slurry was then ground in a 4-L Waring commercial heavy-duty blender set at 90% speed for 2 minutes. The finely ground slurry (containing fiber and mill starch) was allowed to settle at 4° C. for 60 minutes. After settling, approximately 1-L water was decanted from the slurry. The remaining slurry was mixed and strained through a 200-mesh sieve (pore size =0.075 mm) placed atop a snug 10-L bucket. The fine-fiber fraction (atop the 200-mesh screen) was removed and mixed with the decant water. This slurry was then strained through the 200-mesh sieve. The fine-fiber fraction was once again removed from atop the 200-mesh screen and mixed with another 500-ml fresh water. The fine-fiber slurry was strained a final time through the 200-mesh sieve. The washed fine-fiber fraction was pressed and scrapped off the sieve using a spatula and placed into a pre-weighed aluminum dish. The fraction was then placed in a large-capacity forced-air oven set at 50° C. and dried for 24 hr. The separated coarse and fine fiber fractions would later be combined, prior to analysis. The remaining mill starch was refrigerated at 4° C. and allowed to settle overnight for 16 hours.

Tabling:

After settling, approximately 1.6-L water was decanted from the mill starch slurry. The remaining slurry was adjusted to a specific gravity of 1.04 and pumped at a rate of 50 ml/minute onto a small-capacity starch table (8'L× 1.75"W) set at a 0.6° pitch. As it was pumped, the starch settled onto the table as the gluten fraction was collected in a 10-L bucket placed at the distal end of the starch table. After the mill starch supply was exhausted, the decant water was pumped onto the table at 50 ml/minute to rinse the starch fraction. The starch was allowed to settle for an additional 10 minutes before another 500-ml fresh water was pumped onto the table at 50 ml/minute to give the starch a final rinse. Simultaneously, another 250-ml water was placed in a squeeze bottle and used to wash any remaining surface protein down the table. The starch was immediately scrapped off the table and dried for 24 hours in a large-capacity forced-air oven set at 50° C.

The gluten fraction was centrifuged at 6000 rpm for 20 minutes. After centrifugation, the rinse water was decanted and analyzed for dissolved solids. The gluten was scrapped out of the centrifuge bottle and placed in a pre-weighed aluminum dish. The fraction was then dried for 24 hours in a large-capacity forced-air oven set at 50° C.

After drying, all fractions were analyzed for moisture content to determine mass-balance on a moisture-free (dry) basis.

Analytical Procedures:

Moisture content of solid fractions was determined, in duplicate, by drying 1-g ground solids in a convection oven at 130° C. for 3 hours (AOAC 1992, method 14.004).

Total solids in steep water was determined by drying the entire sample in a large-capacity forced-air oven set at 50° C. for 24 hr followed by drying in a convection oven at 130° C. for 3 hr (AOAC 1992, method 14.004).

Dissolved solids in rinse water was determined, in duplicate, by drying a 100-ml sample (in duplicate) in a large-capacity forced-air oven set at 50° C. for 24 hr followed by drying in a convection oven at 130° C. for 3 hr (AOAC 1992, method 14.004).

Total mass balance for all fractions was determined on a moisture-free (dry weight) basis.

This was the procedure used in the present example for wet-milling. Any modification could be included by the one skilled in the art. Any other procedure could be used.

For example, an alternative germ separation technique could be used, such as germ flotation (commonly used for larger sample runs (1 kg and above)). Alternative to coarse grinding in a Waring Blender, the kernels may be cracked by coarse grinding in a Sprout-Bauer mill and added to a substantial volume of water. The germ is separated and removed by flotation.

Example 6

Grain Properties Determination

Maize lines (transgenic and non-transgenic) have been analyzed for their grain properties according to methods known by the one skilled in the art. These methods are commonly used for these kinds of analysis.

Results:

It appears, unexpectedly, that maize grains from the transgenic lines (transformed with puroindoline-a (BW+) or puroindoline-b genes (BU+)) had different grain properties with regard to the wild-type maize grains (non-transgenic), in particular concerning the oil content.

The maize lines that integrated the puroindoline-a or puroindoline-b genes had an oil content higher than wild-type maize lines.

TABLE 4

Grain Properties

| Compositional/Physical Property | Sample and Steep Time (hr) | | | | | | | |
|---|---|---|---|---|---|---|---|---|
| | BU+ (24) | BU+ (40) | BW+ (24) | BW+ (40) | BU− (24) | BU− (40) | BW− (24) | BW− (40) |
| NIR Moisture Content (%) | 12.0 | 11.8 | 12.4 | 12.4 | 12.4 | 11.4 | 12.4 | 12.1 |
| NIR Protein Content (%, dry basis) | 15.1 | 13.5 | 14.6 | 14.6 | 14.6 | 15.3 | 14.6 | 14.8 |
| NIR Starch Content (%, dry basis) | 61.8 | 63.0 | 63.1 | 63.1 | 63.5 | 62.3 | 63.5 | 63.8 |
| NIR Oil Content (%, dry basis) | 6.02 | 5.79 | 5.48 | 5.48 | 5.02 | 4.63 | 4.34 | 4.32 |

REFERENCES

An et al. (1986), *Plant Physiology*, 81:86-91
Anderson O. D. et al. (1989), Theor Appl Genet, 77: 689-700
Allison et al. (1986); the MDMV leader (Maize Dwarf Mozaic Virus), *Virology*, 154:9-20
Armstrong et al., (1994), Maize handbook; M. Freeling, V. walbot Eds, 665-671
Berg et al., (1983)
Bevan et al. (1983), *Nature*, 304:184-187
Bevan et al. (1984) *Nucleic Acid Research*, 11, 369-385
Callis et al. (1987), *Genes Dev.*, 1:1183
Cao J., Duan, X., McElroy, D. and Wu, R. (1992) *Plant Cell. Rep.* 11, 586-591.
Carrington and Freed (1990), J. virol. 64(4):1590-1597
Christensen et al. (1996), Transgenic. Res., 5:213
Davies and Smith (1978)
Dekeyser et al. (1988), *Plant Physiology*, 90:217-223
Della-Cioppa et al. (1987), *Plant Physiology*, 84:965-968
Depicker et al., (1982) *J. Mol. Appl. Genet.*, 1, 561-573
Depicker et al. (1992), *Mol. Gen. Genet.*, 235(2-3):389-396
Depigny-This et al. (1992), *Plant Molecular Biology*, 20:467-479
Donn et al., 1984, J. Mol. Appl. Genet. 2:549-562
Eichholtz et al. (1987), *Somatic Cell and Molecular Genetics*, 13:67-76
Elroy-Stein, O., Fuerest, T. R., and Moss B. (1989), *PNAS USA*, 86:6126-6130
Fraley et al. (1983), *Proc. Natl. Acad. Sci.* USA 80:4803
Franck et al. (1980), *Cell*, 21(1):285-94
Fromm et al.(1985), "Expression of Genes Transferred into Monocot and Dicot Plant Cells by Electroporation", *Proc. Natl Acad. Sci.* USA 82:5824
Gallie, D. R. et al. (1989), *Molecular Biology of RNA*, pages 237-256
Gautier M-F et al (1994), *Triticum aestivum* puroindolines, two basic cystine-rich seed proteins: cDNA sequence analysis and developmental gene expression, *Plant Molecular Biology*, 25:43-57
Giroux M. J. and Morris C. F.(1998), Wheat grain hardness results from highly conserved mutations in the friabilin components puroindoline a and b, *Proc. Natl. Acad. Sci.* USA, 95(11) pp 6262-6266
Gritz et al. (1983), *Gene*, 25:179-188
Halford, N. et al. (1989) Functional analysis of the upstream regions of a silent and a expressed member of a family of wheat seed protein genes in transgenic tobacco. *Plant Science* 62:207-216
Hauptmann et al. (1988), *Plant Physiology*, 86:602-606
Herrera-Estrella et al. (1983), *EMBO Journal* 2:987-995
Hiei et al. (1994) The Plant Journal, 6:271-282
Hoekema et al. (1983) Nature, 303:179-180
Hohn et al. (1982), "Molecular Biology of Plant Tumors", Academic Press, New York, pp.549-560
Horsch et al. (1984), "Inheritance of Functional Foreign Genes in Plants", *Science*, 233:496-498
Howell, U.S. Pat. No. 4,407,956
Ishida et al., (1996), Nature biotechnology, 14, 745-750
Jobling, S. A., and Gehrke, L. (1987), *Nature*, 325:622-625
Jouanin et al. (1987), *Plant Science*, 53:53-63
Kay et al. (1987), *Science*, 236:1299-1302
Lommel, S. A. et al. (1991), *Virology*, 81:382-385
Maas et al. (1991), *Plant Molecular Biology*, 16:199
Macejack, D. G., and P. Sarnow (1991), *Nature*, 353:90-94
Mattanovitch et al. Nucleic Acids Research (1989), 17 (16): 6747
McCormick et al. (1986), *Plant Cell Reports*, 5:81-84
McElroy et al. (1990), *Plant Cell*, 2:163-171
McElroy D., Blowers, A. D., Jenes, B. and Wu, R. (1991) *Mol. Gen. Genet.* 231, 150-160.
Meijer et al. (1991), *Plant Molecular Biology*, 16:807-820
Morris et al. (1992), *Virology*, 187:633
Mullis, K B (1987), *Methods in Enzymology* 155:335
Ohta et al. (1990), *Plant Cell Physiology*, 31:805
Paszkowski et al. (1984), *EMBO Journal* 3:2717-22

Roberts et al. (1989), *Plant cell*, 1:569-578
Sambrook et al. (1989), *Molecular Cloning, A Laboratory Manual*, Cold Spring Harbour Laboratory Press p. 9.54-9.62
Snowdon et al. (1996), *Plant Molecular Biology*, 31:689
Southern, E M (1975), *Journal of Molecular Biology*, 98:503
Vancanneyt et al. (1990), *Molecular and General Genetics*, 220:245-250
Vain et al., (1989), Plant Cell Tissue and Organ Culture, 18, 143-151
Waldron et al. (1985), *Plant Molecular Biology* 5:103-108
White, J., Chang S-Y P., Bibb, M J and Bibb, M J (1990) Nuci. Acid. Res. 18, 1062.
Wu and Grossman (1987) Eds., Academic Press *Methods in Enzymology* Vol. 153 ("Recombinant DNA Part D")
Yoder et al., (1993) Biotechnology, 12, 263-292.
Zambrisky et al. (1989) Cell, 56, 193-201

---

The invention claimed is:

1. A method for obtaining corn with improved starch extractability comprising the step of transforming a maize plant with a nucleic acid sequence encoding a wheat puroindoline-a protein, a nucleic acid sequence encoding a wheat puroindoline-b protein or both a nucleic acid sequence encoding a wheat puroindoline-b protein and a nucleic acid sequence encoding a wheat puroindoline-a protein, wherein said nucleic acid sequence or nucleic acid sequences are under control of the wheat HMWG promoter, thereby obtaining corn with improved starch extractability.

2. The method of claim 1 wherein said nucleic acid sequence encodes the puroindoline-b protein of SEQ ID NO: 2.

3. The method of claim 1 wherein said nucleic acid sequence encodes the puroindoline-a protein of SEQ ID NO: 4.

4. A method of improving starch extractability comprising the steps of
 a. cultivating a maize plant transformed with a nucleic acid sequence encoding a wheat puroindoline-b protein, a nucleic acid sequence encoding a wheat puroindoline-a protein or both, and
 b. harvesting corn produced by said maize plant, wherein said transformed maize plant is obtained by introducing a nucleic acid sequence encoding a wheat puroindoline-b protein, a nucleic acid sequence encoding a wheat puroindoline-a protein, or nucleic acid sequences encoding a wheat puroindoline-b protein and a wheat puroindoline-a protein into at least a maize cell, wherein said nucleic acid sequence or nucleic acid sequences are under control of the wheat HMWG promoter, and cultivating such transformed cell under conditions for regenerating a fertile stable transformed maize plant.

5. The method of claim 4, wherein said maize plant is transformed with a nucleic acid sequence encoding a wheat puroindoline-b protein.

6. The method of claim 4 wherein said maize plant is transformed with a nucleic acid sequence encoding a wheat puroindoline-a protein.

7. The method of claim 4 wherein said maize plant is transformed with a nucleic acid sequence encoding a wheat puroindoline-b protein and a nucleic acid sequence encoding a wheat puroindoline-a protein.

* * * * *